(12) United States Patent
Steiner et al.

(10) Patent No.: US 6,387,912 B1
(45) Date of Patent: May 14, 2002

(54) UTILIZATION OF PYRIMIDINE DERIVATIVES FOR PREVENTING AND TREATING CEREBRAL ISCHAEMIA

(75) Inventors: Gerd Steiner, Kirchheim; Kurt Schellhaas, Ludwigshafen; Wilfried Lubisch, Heidelberg; Uta Holzenkamp, Lambsheim; Dorothea Starck; Monika Knopp, both of Ludwigshafen; Laszlo Szabo, Dossenheim; Franz Emling, Ludwigshafen; Francisco Javier Garcia-Ladona, Kandel; Hans-Peter Hofmann, Limburgerhof; Liliane Unger, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,162

(22) PCT Filed: Dec. 24, 1999

(86) PCT No.: PCT/EP99/10369

§ 371 Date: Jul. 11, 2001

§ 102(e) Date: Jul. 11, 2001

(87) PCT Pub. No.: WO00/41695

PCT Pub. Date: Jul. 20, 2000

(30) Foreign Application Priority Data

Jan. 11, 1999 (DE) .......................................... 199 00 545

(51) Int. Cl.$^7$ ...................... A61K 31/513; A61K 31/519

(52) U.S. Cl. .................. 514/258; 514/267; 514/217.06; 514/211.08

(58) Field of Search ................................ 514/258, 267, 514/217.06, 211.08

(56) References Cited

FOREIGN PATENT DOCUMENTS

| | | |
|---|---|---|
| DE | 196 36 769 | 3/1998 |
| DE | 197 24 979 | 12/1998 |
| DE | 197 24 980 | 12/1998 |
| EP | 0 244 176 | 11/1987 |
| WO | WO 98/11110 | 3/1998 |
| WO | WO 98/56792 | 12/1998 |
| WO | WO 98/56793 | 12/1998 |

*Primary Examiner*—John M. Ford
(74) *Attorney, Agent, or Firm*—Keil & Weinkauf

(57) ABSTRACT

Use of pyrimidine derivatives of the formula I

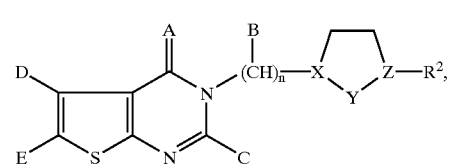

where the substituents are as defined in the description, and of their physiologically tolerated salts for producing medicaments for the prophylaxis and treatment of cerebral ischemia and strokes.

1 Claim, No Drawings

UTILIZATION OF PYRIMIDINE DERIVATIVES FOR PREVENTING AND TREATING CEREBRAL ISCHAEMIA

This is a 371 of PCT/EP99/10369 filed Dec. 24, 1999.

The invention relates to the use of pyrimidine derivatives for the prophylaxis and therapy of cerebral ischemia.

DE 1936769.7 describes 3-substituted 3,4,5,6,7,8-hexahydro-pyrido [4',3':4,5] thieno [2,3-d] pyrimidine derivatives of the formula I

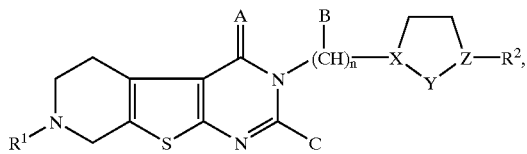

where
- $R^1$ is hydrogen, a $C_1$–$C_4$-alkyl group, an acetyl or benzoyl group, a phenylalkyl $C_1$–$C_4$ radical, with the aromatic moiety optionally being substituted by halogen, or $C_1$–$C_4$-alkyl, trifluoromethyl, hydroxyl, $C_1$–$C_4$-alkoxy, amino, cyano or nitro groups, a naphthylalkyl $C_1$–$C_3$ radical, a phenylalkanone $C_2$–$C_3$ radical or a phenyl-carbamoylalkyl $C_2$ radical, with it being possible for the phenyl group to be substituted by halogen,
- $R^2$ is a phenyl, pyridyl, pyrimidinyl or pyrazinyl group which is optionally monosubstituted, disubstituted or trisubstituted by halogen atoms, $C_1$–$C_4$-alkyl or trifluoromethyl, trifluoromethoxy, hydroxyl, $C_1$–$C_4$-alkoxy, amino, monomethylamino, dimethylamino, cyano or nitro groups and which can optionally be fused to a benzene nucleus which can optionally be monosubstituted or disubstituted by halogen atoms, $C_1$–$C_4$-alkyl or hydroxyl, trifluoromethyl, $C_1$–$C_4$-alkoxy, amino, cyano or nitro groups and can optionally contain 1 nitrogen atom, or to a 5- or 6-membered ring which can contain 1–2 oxygen atoms, or can be optionally substituted by a phenyl-$C_1$–$C_2$-alkyl- or alkoxy group, with it being possible for the phenyl radical to be substituted by halogen, or a methyl, trifluoromethyl or methoxy group,
- A is NH or oxygen,
- B is hydrogen or methyl,
- C is hydrogen, methyl or hydroxyl,
- X is nitrogen,
- Y is $CH_2$, $CH_2$—$CH_2$, $CH_2$—$CH_2$—$CH_2$ or $CH_2$—$CH$,
- Z is nitrogen, carbon or CH, with it also being possible for the bond between Y and Z to be a double bond,
- and n is the number 2, 3 or 4.

These compounds of the formula I can be prepared by reacting a compound of the formula II

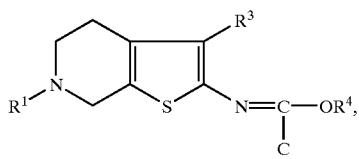

in which $R^1$ has the abovementioned meaning, $R^3$ is a cyano group or a $C_{1-3}$-alkyl-carboxylic ester group, $R^4$ is $C_{1-3}$-alkyl and C is hydrogen, methyl or hydroxyl, with a primary amine of the formula III

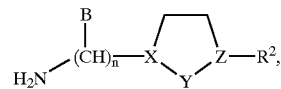

where $R^2$ and B have the abovementioned meanings, and, where appropriate, converting the resulting compound into the acid addition salt of a physiologically tolerated acid.

The reaction expediently takes place in an inert organic solvent, in particular a lower alcohol, e.g. methanol or ethanol, or a cyclic, saturated ether, in particular tetrahydrofuran or dioxane, or without any solvent.

As a rule, the reaction takes place at from 20 to 190° C., in particular from 60 to 90° C., and has generally finished within from 1 to 10 hours.

Or, a compound of the formula II

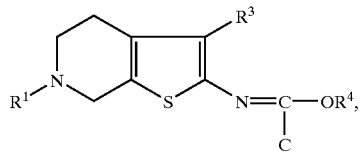

where $R^1$ has the abovementioned meanings, $R^3$ is a cyano group or a $C_{1-3}$-alkyl-carboxylic ester group, $R^4$ is $C_{1-3}$-alkyl and C is hydrogen, methyl or hydroxy, is reacted with a primary amine of the formula IV

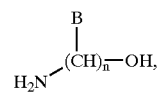

where B has the abovementioned meanings, in an inert solvent, preferably alcohols, such as ethanol, at from 60 to 120° C., to give the cyclization product V (D=OH)

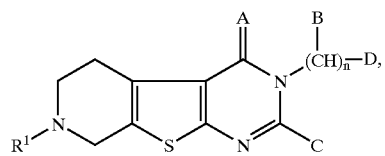

which is then converted with a halogenating agent, such as thionyl chloride or hydrobromic acid, in an organic solvent such as a halogenohydrocarbon, or without any solvent, at from room temperature to 100° C., into the corresponding halogen derivative V (D=Cl, Br). Finally, the halogen derivative of the formula V (D=Cl, Br) is reacted with an amine of the formula VI

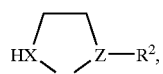

where X, Y, Z and $R^2$ have the abovementioned meanings, to give the novel end product of the formula I. This reaction proceeds most efficiently in an inert organic solvent, preferably toluene or xylene, in the presence of a base, such as potassium carbonate or potassium hydroxide, and at from 60 to 150° C.

The novel compounds of the formula I can be purified either by recrystallization from the customary organic solvents, preferably from a lower alcohol, such as ethanol, or by means of column chromatography.

The free 3-substituted pyrido[4',3':4, 5]thieno[2,3-d]-pyrimidine derivatives of the formula I can be converted, in the customary manner, into the acid addition salts of a solution using the stoichiometric quantity of the corresponding acid. Examples of pharmaceutically tolerated acids are hydrochloric acid, phosphoric acid, sulfuric acid, methanesulfonic acid, amidosulfuric acid, maleic acid, fumaric acid, oxalic acid, tartaric acid or citric acid.

The following Examples serve to clarify the invention:

A Preparation of the starting materials of the formulae II, V and VI

The 2-amino-3-carboethoxy(cyano)-4,5,6,7-tetrahydrothieno-[2,3-c]pyridines having a methyl, benzyl, acetyl or benzoyl group in the 6 position or having a 6 position which is unsubstituted, which are employed as starting materials, are known from the literature (K. Gewald et al.).

a) 2-Ethoxymethyleneamino-3-cyano-6-methyl-4,5,6,7-tetrahydrothieno[2,3-c]pyridine 3.5 ml of acetic anhydride were added to 46.0 g (238 mmol) of 2-amino-3-cyano-6-methyl-4,5,6,7-tetrahydrothieno[2,3-c]-pyridine in 250 ml of triethyl orthoformate and the mixture was boiled under nitrogen and at reflux for 4 h. After that, the mixture was filtered off with suction, in the hot, through a suction filter and the filtrate was evaporated right down at 80° C. on a rotary evaporator. The residue was taken up in 300 ml of methyl t-butyl ether and this mixture was heated to boiling. After the insoluble solids had been filtered off with suction, 45.4 g (77%) of the product crystallized out in an icebath with stirring. A further 1.7 g (3%) of product were obtained from the mother liquor as a second fraction. m.p.: 88–89° C.

b) 2-Ethoxymethyleneamino-3-carboethoxy-6-methyl-4,5,6,7-tetrahydrothieno[2,3-c]pyridine 3.2 ml of acetic anhydride were added to 40.0 g (167 mmol) of 5 2-amino-3-carboethoxy-6-methyl-4,5,6,7-tetrahydrothieno-[2,3-c]pyridine in 250 ml of triethyl orthoformate and the mixture was boiled under nitrogen and at reflux for 3 h. After that, the mixture was evaporated right down at 80° C. on a rotary evaporator. 48.0 g (97%) of crude product were isolated as a dark oil, which is sufficiently pure for further reaction.

c) 2-Amino-3-carboethoxy-6-(4-chloro)benzyl-4,5,6,7-tetrahydrothieno[2,3-c]pyridine 25.6 g (204 mmol) of 4-chlorobenzyl chloride and 12.4 g (90 mmol) of finely powdered potassium carbonate were added to 20.4 g (90.2 mmol) of 2-amino-3-carboethoxy-4,5,6,7-tetrahydrothieno[2,3-c]pyridine in 250 ml of tetrahydrofuran and the mixture was boiled at reflux for 3 h. After that, the mixture was evaporated right down on a rotary evaporator. The residue was partitioned between methyl t-butyl ether and water, after which the phases were rendered alkaline with sodium hydroxide solution and the organic phase was then washed with water and evaporated. The crude product was dissolved in 100 ml of hot ethanol and was left to crystallize while stirring. 20.5 g (65%) of product having a m.p. of 134–135° C. were isolated.

d) 2-Ethoxymethyleneamino-3-carboethoxy-6-(4-chloro) benzyl-4,5,6,7-tetrahydrothieno[2,3-c]pyridine 2.0 ml of acetic anhydride were added to 19.3 g (55.0 mmol) of 2-amino-3-carboethoxy-6-(p-chlorobenzyl)-4,5,6,7-tetrahydrothieno[2,3-c]pyridine in 125 ml of triethyl orthoformate and the mixture was boiled under nitrogen and at reflux for 1 h. After that, the mixture was evaporated right down at 80° C. on a rotary evaporator. 21.9 g (98%) of crude product were isolated as a dark oil, which is sufficiently pure for further reaction.

e) 2-Amino-3-carboethoxy-6-(3-phenyl)propyl-4,5,6,7-tetrahydrothieno[2,3-c]pyridine 9.0 g (45 mmol) of 1-phenyl-3-bromopropane, 400 mg of potassium iodide and 6.1 g (44.2 mmol) of finely powdered potassium carbonate were added to 10.0 g (44.2 mol) of 2-amino-3-carboethoxy-4,5,6,7-tetrahydrothieno[2,3-c)pyridine in 100 ml of xylene and the mixture was boiled at reflux for 6 h. Following evaporation on a rotary evaporator, the residue was taken up in water and this mixture was adjusted to pH=10 and extracted twice with methylene chloride. After the organic phase had been dried and evaporated, the crude product was thoroughly stirred in 50 ml of isopropanol. The pale solids were filtered off with suction and rewashed with isopropanol. 7.8 g (51%) of product having a m.p. of 108–110° C. were isolated.

The additional 4,5,6,7-tetrahydrothieno[2,3-c]pyridine derivatives which are substituted in the 6 position were prepared in analogy with c) and e), e.g.:

2-Amino-3-carboethoxy-6-ethyl-4,5,6,7-tetrahydrothieno-[2,3-c]pyridine, m.p. 74–76° C.

2-Amino-3-carboethoxy-6-isopropyl-4,5,6,7-tetrahydrothieno [2,3-c]pyridine

2-Amino-3-carboethoxy-6-benzyl-4,5,6,7-tetrahydrothieno-[2,3-c]pyridine, m.p. 116–118° C.

2-Amino-3-carboethoxy-6-(4-methyl)benzyl-4,5,6,7-tetrahydrothieno[2,3-c]pyridine 2-Amino-3-carboethoxy-6-(4-nitro)benzyl-4,5,6,7-tetrahydrothieno[2,3-c]pyridine, m.p. 170–172° C.

2-Amino-3-carboethoxy-6-(4-methoxy)benzyl-4,5,6,7-tetrahydrothieno[2,3-c]pyridine, m.p. 154–156° C.

2-Amino-3-carboethoxy-6-(2-phenyl)ethyl-4,5,6,7-tetrahydrothieno[2,3-c]pyridine, m.p. 80–83° C.

2-Amino-3-carboethoxy-6-(2-(4-methoxyphenyl)ethyl)-4,5,6,7-tetrahydrothieno[2,3-c]pyridine, m.p. 76–78° C.

2-Amino-3-carboethoxy-6-(2-(4-chlorophenyl)ethyl)-4,5,6,7-tetrahydrothieno[2,3-c]pyridine, m.p. 102–105° C.

2-Amino-3-carboethoxy-6-(3-(4-chloro)phenyl)propyl-4,5,6,7-tetrahydrothieno[2,3-c]pyridine 2-Amino-3-carboethoxy-6-(4-phenyl)butyl-4,5,6,7-tetrahydrothieno[2,3-c]pyridine 2-Amino-3-carboethoxy-6-(3-benzoyl)propyl-4,5,6,7-tetrahydrothieno[2,3-c]pyridine 2-Amino-3-carboethoxy-6-(2-benzoylamino)ethyl-4,5,6,7-tetrahydrothieno[2,3-c]pyridine, m.p. 190–192° C.

2-Amino-3-carboethoxy-6-(2-(N-benzoyl)aminoethyl)-4,5,6,7-tetrahydrothieno[2,3-c]pyridine 2-Amino-3-carboethoxy-6-(3-benzoylamino)propyl-4,5,6,7-tetrahydrothieno[2,3-c]pyridine f) Ethyl N-(3-carboethoxy-6-methyl-4,5,6,7-tetrahydrothieno-[2,3-c]pyridin-2-yl)ethaneimidate 0.8 ml of acetic anhydride was added to 3.0 g (12.5 mmol) of 2-amino-3-carboethoxy-4,5,6,7-tetrahydrothieno[2,3-c]pyridine in 25 ml of triethyl orthoacetate and the mixture was boiled under nitrogen and at reflux for 2 h. After that, the mixture was evaporated right down at 80° C. on a rotary evaporator. 3.6 g (93%) of crude product were isolated as a dark oil, which is sufficiently pure for further reaction.

g) 2-Carboethoxyamino-3-carboethoxy-6-acetyl-4,5,6,7-tetrahydrothieno[2,3-c]pyridine 3.0 g (28 mmol) of ethyl chloroformate and 2.6 g (18.6 mmol) of finely powdered potassium carbonate were added to 5.0 g (18.6 mmol) of 2-amino-3-carboethoxy-6-acetyl-4,5,6,7-tetrahydrothieno-[2,3-c]pyridine in 50 ml of toluene and the mixture was boiled at reflux for 2 h. After that, the reaction mixture was taken up in ice/water, after which the toluene phase was separated off and the aqueous phase was reextracted with toluene. After drying, the combined organic phases were evaporated. 5.8 g (92%) of product were isolated as an oil, which slowly crystallizes to some degree.

h) 3,4,5,6,7,8-Hexahydro-3-(2-hydroxy)ethyl-7-methylpyrido-[4',3':4,5]thieno[2,3-d]pyrimidin-4-one 17.6 ml (292 mmol) of ethanolamine were added to 86.4 g (292 mmol) of 2-ethoxymethyleneamino-3-carboethoxy-6-methyl-4,5,6,7-tetrahydrothieno[2,3-c]pyridine in 200 ml of ethanol and the mixture was boiled at reflux for 2 h. The mixture was then evaporated in vacuo and the residue was taken up in 30 ml of ethyl acetate while stirring. The solids which precipitated out overnight were filtered off with suction and rewashed with a little ethyl acetate. After recrystallizing from ethanol, 48.0 g (62%) of product having a m.p. of 163–165° C. were isolated.

2,4,5,6,7,8-Hexahydro-3-(2-chloro)ethyl-7-methylpyrido-[4',3':4,5]thieno[2,3-d]pyrimidin-4-one 42.0 g (158 mmol) of 3,4,5,6,7,8-hexahydro-3-(2-hydroxy)-ethyl-7-methylpyrido[4',3':4,5]thieno[2,3-d]pyrimidin-4-one in 240 ml of 1,2-dichloroethane were heated to reflux, after which 12.7 ml (175 mmol) of thionyl chloride in 20 ml of 1,2-dichloroethane were added dropwise. After 2 h of boiling at reflux, the reaction mixture was allowed to cool and was poured onto ice/water. The mixture was partitioned, at pH=10, between methylene chloride and water, and the aqueous phase was reextracted with methylene chloride. After drying, the combined organic phases were evaporated. The crude product (40 g) was recrystallized from 400 ml of isopropanol. 30.5 g (68%) of product having a m.p. of 159–161° C. were isolated.

The following were prepared in analogy with h) and i):

3,4,5,6,7,8-Hexahydro-3-(1-hydroxy)prop-2-yl-7-methylpyrido[4',3':4,5]thieno[2,3-d]pyrimidin-4-one 3,4,5,6,7,8-Hexahydro-3-(1-chloro)prop-2-yl-7-methylpyrido-[4',3':4,5]thieno[2,3-d]pyrimidin-4-one 3,4,5,6,7,8-Hexahydro-3-(2-hydroxy)propyl-7-methylpyrido-[4',3':4,5]thieno[2,3-d]pyrimidin-4-one, m.p. 158–160° C.

3,4,5,6,7,8-Hexahydro-3-(2-chloro)propyl-7-methylpyrido-[4',3':4,5]thieno[2,3-d]pyrimidin-4-one k) N-(1-Naphthyl)piperazine 83.2 g (966 mmol) of piperazine, 38.0 g (339 mmol) of potassium tert-butoxide and 50.0 g (241 mmol) of 1-bromonaphthalene were added to a mixture of 5.4 g (24.2 mmol) of palladium acetate and 14.7 g (48.3 mmol) of tri-o-tolylphosphine in 500 ml of xylene and the reaction mixture was heated at reflux for 10 h under a nitrogen atmosphere and while stirring thoroughly. After that, the mixture was diluted with methylene chloride, the insoluble residues were filtered off and the filtrate was evaporated. The crude product was purified by column chromatography (silica gel, eluent THF/methanol/ammonia 85/13/2). 21.5 g (42%) of product having a m.p. of 84–86° C. were isolated.

l) N-(2-Methyl-1-naphthyl)piperazine 14.7 g (82.7 mmol) of bis(2-chloroethyl)amine×HCl were added to 13.0 g (82.7 mmol) of 1-amino-2-methylnaphthalene in 100 ml of chlorobenzene and the mixture was boiled under nitrogen and at reflux for 90 h. The mixture was then evaporated and the residue was partitioned between methylene chloride and water at pH=9, and the organic phase was evaporated after having been dried. The crude product was purified by column chromatography (silica gel, eluent THF/methanol/ammonia, 85/13/2). 11.6 g (62%) of product were isolated.

m) 4-Piperazin-1-ylisoquinoline 4.51 g (21.7 mmol) of 4-bromoisoquinoline, 4.65 g (25.0 mmol) of t-butyl piperazine-N-carboxylate, 0.1 g (0.11 mmol) of tris(dibenzylideneacetone)dipalladium, 0.11 g (0.18 mmol) of 2,2'-bis(diphenylphosphino)-1,1'-binaphthyl and 2.92 g (30.4 mmol) of sodium t-butoxide were together added to 50 ml of toluene and the mixture was stirred at 75° C. for 2 h. The reaction mixture was added to ice/sodium chloride and the latter mixture was extracted with ethyl acetate; the organic phase was dried over sodium sulfate and the solvent was removed on a rotary evaporator. The product crystallized out and was filtered off with suction and washed with pentane. This resulted in 5.5 g (81%) of the Boc-protected piperazine (m.p.: 111° C.). 5.2 g (16.6 mmol) of this substance were taken up in 17 ml of dichloromethane, after which 17 ml (0.22 mmol) of trifluoroacetic acid were slowly added at 0° C. The mixture was left to stir at 0° C. for 4 h and was then poured onto ice water and this latter mixture was extracted with dichloromethane. The aqueous phase was filtered, rendered alkaline and extracted with dichloromethane. After drying over sodium sulfate and to a large extent removing the solvent, dilution was carried out with diethyl ether, and the hydrochloride was precipitated with ethereal hydrochloric acid. This afforded 3.2 g (67%) of the product having a m.p. of 293–294° C.

Insofar as they were not known from the literature (cf. Patent Application DE 19636769.7 as well), additional piperazine derivatives (see Examples) were prepared in analogy with k), l) and m).

B Preparation of the end products

EXAMPLE 1

3,4,5,6,7,8-Hexahydro-7-methyl-3-[2-(4-(2-methoxyphenyl)-piperazin-1-yl)ethyl]pyrido[4',3':4,5]thieno[2,3-d]pyrimidin-4-imine×3 HCl 3.3 g (12.1 mmol) of 1-(2-aminoethyl)-4-(2-methoxyphenyl)-piperazine were added to 3.0 g (12.1 mmol) of 2-ethoxymethylene-amino-3-cyano-6-methyl-4,5,6,7-tetrahydrothieno[2,3-c]pyridine in 60 ml of ethanol and the mixture was boiled at reflux for 3 h. After that, the mixture was evaporated on a rotary evaporator and the residue was taken up in 100 ml of ethyl acetate. The trihydrochloride was precipitated, while stirring, by adding ethereal hydrochloric acid, after which the product was filtered off with suction under nitrogen and was rewashed with ethyl acetate. After drying at 50° C. in a vacuum cabinet, 3.6 g (55%) of product having a decomposition point of 282–284° C. were isolated.

EXAMPLE 2

3,4,5,6,7,8-Hexahydro-7-methyl-3-[2-(4-(2-methoxyphenyl)-piperazin-1-yl)ethyl]pyrido[4',3':4,5]thieno[2,3-d]pyrimidin-4-one×3 HCl 2.4 g (10.2 mmol) of 1-(2-aminoethyl)-4-(2-methoxyphenyl)-piperazine were added to 3.0 g (12.1 mmol) of 2-ethoxymethylene-amino-3-carboethoxy-6-methyl-4,5,6,7-tetrahydrothieno[2,3-c]-pyridine in 50 ml of ethanol and the mixture was boiled at reflux for 3 h. After that, the mixture was evaporated on a rotary evaporator and the crude product was purified by column chromatography (silica gel, eluent methylene chloride/methanol, 93/7). The free base was converted into the trichloride (3.2 g, 48%), having a decomposition point of 288–290° C., as above.

EXAMPLE 3

3,4,5,6,7,8-Hexahydro-7-(4-chlorobenzyl)-3-[2-(4-(2-methoxyphenyl)piperazin-1-yl)ethyl]pyrido[4',3':4,5]thieno[2,3-d]pyrimidin-4-one×3 HCl 2.0 g (8.6 mmol) of 1-(2-aminoethyl)-4-(2-methoxyphenyl)-piperazine were added to 3.5 g (8.6 mmol) of 2-ethoxymethylene-amino-3-carboethoxy-6-(4-chlorobenzyl)-4,5,6,7-tetrahydrothieno [2,3-c]pyridine in 60 ml of ethanol and the mixture was boiled at reflux for 4 h. After that, the mixture was evaporated on a rotary evaporator and the crude product was purified by column chromatography (silica gel, eluent methylene chloride/methanol 95/5). The free base was converted into the trihydrochloride (3.2 g, 57%), having a decomposition point of 290–293° C., as above.

EXAMPLE 4

3,4,5,6,7,8-Hexahydro-7-methyl-3-[3-(4-(2-methoxyphenyl)-piperazin-1-yl)propyl]pyrido[4',3':4,5]thieno[2,3-d]pyrimidin-4-one×3 HCl×2 $H_2O$ 3.0 g (11.8 mmol) of 1-(3-aminopropyl)-4-(2-methoxyphenyl)-piperazine were added to 3.5 g (11.8 mmol) of 2-ethoxymethylene-amino-3-carboethoxy-6-methyl-4,5,6,7-tetrahydrothieno[2,3-c]pyridine in 40 ml of ethanol and the mixture was boiled at reflux for 2 h. After that, the mixture was evaporated on a rotary evaporator and the crude product was purified by column chromatography (silica gel, eluent methylene chloride/methanol 93/7). The free base was converted into the trihydrochloride (3.1 g, 44%), having a decomposition point of 122–124° C., as above.

EXAMPLE 5

3,4,5,6,7,8-Hexahydro-7-methyl-3-[3-(4-pyridin-2-yl)piperazin-1-yl)propyl]pyrido[4',3':4,5]thieno[2,3-d]pyrimidin-4-imine×4 HCl×$H_2O$ 2.65 g (12.1 mmol) of 1-(3-aminopropyl)-4-pyridin-2-yl-piperazine were added to 3.0 g (12.1 mmol) of 2-ethoxymethylene-amino-3-cyano-6-methyl-4,5,6,7-tetrahydrothieno[2,3-c]pyridine in 60 ml of ethanol and the mixture was boiled at reflux for 6 h. After that, the mixture was evaporated on a rotary evaporator and the crude product was taken up in 100 ml of ethyl acetate. The solids which crystallized overnight were converted into the tetrahydrochloride, as above. 2.7 g (38%) of product having a decomposition point of 261–264° C. were isolated.

EXAMPLE 6

3,4,5,6,7,8-Hexahydro-7-methyl-3-[3-(4-(2-thiomethylphenyl)-piperazin-1-yl)propyl]pyrido[4',3':4,5]thieno[2,3-d]pyrimidin-4-imine×3 HCl 3.2 g (12.1 mmol) of 1-(3-aminopropyl)-4-(2-thiomethylphenyl)-piperazine were added to 3.0 g (12.1 mmol) of 2-ethoxymethylene-amino-3-cyano-6-methyl-4,5,6,7-tetrahydrothieno[2,3-c]pyridine in 50 ml of ethanol and the mixture was boiled at reflux for 4 h. After that, the mixture was evaporated on a rotary evaporator and the residue was taken up in 100 ml of ethyl acetate while heating to boiling. After cooling, the insoluble constituents were filtered off and the trihydrochloride was precipitated in the filtrate, while stirring, by adding ethereal hydrochloric acid; the product was filtered off with suction under nitrogen and rewashed with ethyl acetate. The crude product (5.1 g) was then recrystallized from methanol. 3.8 g (54%) of product having a m.p. of 306–307° C. were isolated.

EXAMPLE 7

3,4,5,6,7,8-Hexahydro-7-methyl-3-[2-(4-pyridin-2-yl-piperazin-1-yl)ethyl]pyrido[4',3':4,5]thieno[2,3-d]pyrimidin-4-one×3HCl×2$H_2O$ 1.6 g (10.0 mmol) of 1-(2-pyridyl)piperazine, 1.4 g (10.0 mmol) of finely powdered potassium carbonate and 400 mg of potassium iodide were added to 2.2 g (7.8 mmol) of 3,4,5,6,7,8-hexahydro-3-(2-chloro)ethyl-7-methylpyrido[4',3':4,5]thieno[2,3-d]-pyridimin-4-one in 50 ml of xylene and the mixture was boiled at reflux for 24 h. After that, the mixture was evaporated on a rotary evaporator and the residue was partitioned between methylene chloride and water at pH=10. The aqueous phase was reextracted once again with methylene chloride and the combined organic phases were evaporated after having been dried. The crude product was purified by column chromatography (silica gel, eluent acetone). This resulted in the isolation of 2.3 g (72%) of product, which was dissolved in 100 ml of ethyl acetate and converted into the hydrochloride, having a m.p. of 233–235° C., using an HCl/ethyl acetate solution.

EXAMPLE 8

3,4,5,6,7,8-Hexahydro-7-methyl-3-[1-(4-(1-naphthyl)piperazin-1-yl)prop-2-yl]pyrido[4',3':4,5]thieno[2,3-d]pyrimidin-4-one×3HCl×2$H_2O$ 2.1 g (10.0 mmol) of 1-(1-naphthyl)piperazine, 1.4 g (10.0 mmol) of finely powdered potassium carbonate and 250 mg of potassium iodide were added to 2.7 g (9.0 mmol) of 3,4,5,6,7,8-hexahydro-3-(1-chloro)prop-2-yl-7-methylpyrido[4',3':4,5]thieno[2,3-d]-pyrimidin-4-one in 50 ml of xylene and the mixture was boiled at reflux for 70 h. After that, the mixture was evaporated on a rotary evaporator and the residue was partitioned between methylene chloride and water at pH=10. The aqueous phase was reextracted once again with methylene chloride and the combined organic phases were evaporated after having been dried. The crude product was purified by column chromatography (silica gel, eluent acetone). This resulted in the isolation of 1.6 g (38%) of product, which was dissolved in ethyl acetate and converted into the hydrochloride, having a m.p. of 242–244° C., using an HCl/ethyl acetate solution.

EXAMPLE 9

3,4,5,6,7,8-Hexahydro-7-methyl-3-[2-(4-(2-methoxyphenyl)-piperazin-1-yl)propyl]pyrido[4',3':4,5]thieno[2,3-d]pyrimidin-4-one×3HCl 3.5 g (18.0 mmol) of 1-(2-methoxyphenyl)piperazine; 1.4 g (10.0 mmol) of finely powdered potassium carbonate and 400 mg of potassium iodide were added to 2.9 g (8.9 mmol) of 3,4,5,6,7,8-hexahydro-3-(2-chloro)propyl-7- methylpyrido[4',3':4,5]thieno-[2,3-d]pyrimidin-4-one in 60 ml of xylene and the mixture was boiled at reflux for 100 h. After that, the mixture was evaporated on a rotary evaporator and the residue was partitioned between methylene chloride and water at pH=10. The aqueous phase was reextracted once again with methylene chloride and the combined organic phases were evaporated after having been dried. The crude product was purified by column chromatography (silica gel, eluent acetone). This resulted in the isolation of 1.0 g (25%) of product, which was dissolved in 100 ml of ethyl acetate and was converted into the hydrochloride, having a m.p. of 190–192° C. (decomp.), using an HCl/ethyl acetate solution.

EXAMPLE 10

3,4,5,6,7,8-Hexahydro-2,7-dimethyl-3-[2-(4-(2-methoxyphenyl)-piperazin-1-yl)ethyl]pyrido[4',3':4, 5]thieno[2,3-d]pyrimidin-4-one 1.5 g (6.2 mmol) of 1-(2-aminoethyl)-4-(2-methoxyphenyl)-piperazine were added to 1.9 g (6.2 nmol) of ethyl N-(3-carboethoxy-6-mathyl-4,5,6,7-tetrahydrothieno[2,3-c]pyridin-2-yl)-ethaneimidate in 30 ml of ethanol and the mixture was boiled at reflux for 7 h. After that, the mixture was evaporated on a rotary evaporator and the residue was taken up in 20 ml of ethyl acetate. 2.1 g of crude product crystallized out overnight and was filtered off with suction and purified by column chromatography (silica gel, eluent methylene chloride/methanol 92/8). 0.8 g (29%) of product was isolated.

EXAMPLE 11

3,4,5,6,7,8-Hexahydro-2-hydroxy-7-acetyl-3-[2-(4-(2-methoxyphenyl)piperazin-1-yl)ethyl]pyrido[4', 3':4,5]thieno[2,3-d]-pyrimidin-4-one 2.5 g (7.3 mmol) of 2-carboethoxyamino-3-carboethoxy-6-acetyl-4,5,6,7-tetrahydrothieno[2,3-c]pyridine and 1.7 g (7.3 mmol) of 1-(2-aminoethyl)-4-(2-methoxyphenyl) piperazine were heated at 180° C. for 2 h under nitrogen and with the melt being thoroughly stirred. After cooling, the crude product was purified by column chromatography (silica gel, eluent methylene chloride/methanol 95/5). 0.7 g (20%) of product having a m.p. of 135–137° C. was isolated.

EXAMPLE 12

3,4,5,6,7,8-Hexahydro-7-acetyl-3-[2-(4-(2-methoxyphenyl)-piperazin-1-yl)ethyl]pyrido[4',3':4, 5]thieno[2,3-d]pyrimidin-4-one 5.5 g (23.4 mmol) of 1-(2-aminoethyl)-4-(2-methoxyphenyl)-piperazine were added to 5.8 g (23.4 nmol) of 2-ethoxymethylene-amino-3-carboethoxy-6-acetyl-4,5,6, 7-tetrahydrothieno[2,3-c]-pyridine in 50 ml of ethanol and the mixture was boiled at reflux for 2 h. After that, the mixture was evaporated on a rotary evaporator and the residue was taken up in 30 ml of ethyl acetate, after which this mixture was heated to boiling and allowed to cool while being stirred. The solids which crystallized out were filtered off with suction, after cooling in an icebath, and rewashed with ethyl acetate. 8.7 g (80%) of product having a m.p. of 170–172° C. were isolated.

EXAMPLE 13

3,4,5,6,7,8-Hexahydro-3-[2-(4-(2-methoxyphenyl) piperazin-1-yl)-ethyl]pyrido[4',3':4,5]thieno[2,3-d] pyrimidin-4-one 4.0 g (8.6 mmol) of 3,4,5,6,7,8-hexahydro-7-acetyl-3-[2-(4-(2-methoxyphenyl)piperazin-1-yl)ethyl]pyrido[4',3':4,5] thieno-[2,3-d]pyrimidin-4-one were dissolved in 80 ml of 10% strength hydrochloric acid and this solution was stirred at a bath temperature of 100° C. for 2 h. After that, the mixture was poured onto ice water and this mixture was rendered alkaline with conc. sodium hydroxide solution and extracted twice with methylene chloride. The combined organic phases were dried and evaporated. This resulted in the isolation of 3.7 g of crude product which was then recrystallized from 50 ml of isopropanol. 2.4 g (66%) of product having a m.p. of 168–170° C. were obtained.

EXAMPLE 14

3,4,5,6,7,8-Hexahydro-7-(2-(1-naphthyl)ethyl)-3-[2-(4-(2-methoxyphenyl)piperazin-1-yl)ethyl]pyrido[4', 3':4,5]thieno-[2,3-d]pyrimidin-4-one×3HCl 0.8 g (3.4 mmol) of 2-bromo-1-naphth-1-ylethane and 0.3 g (2.4 mmol) of finely powdered potassium carbonate were added to 1.0 g (2.3 mmol) of 3,4,5,6,7,8-hexahydro-3-[2-(4-(2-methoxyphenyl)piperazin-1-yl)ethyl]pyrido[4',3':4,5] thieno-[2,3-d]pyrimidin-4-one in 35 ml of xylene and the mixture was boiled at reflux for 12 h. After that, the mixture was evaporated on a rotary evaporator and the residue was partitioned at pH=10 between methylene chloride and water. The aqueous phase was reextracted once again with methylene chloride. The combined organic phases were evaporated after having been dried. 2.7 g of crude product were obtained as a dark oil which was purified by column chromatography (silica gel, eluent methylene chloride/ acetone 7/3). After conversion into the hydrochloride in ethyl acetate, 1.0 g (63%) of product having a m.p. of 293–295° C. (decomp.) was isolated.

The following were prepared in analogy with Examples 1 to 14:

15. 3,4,5,6,7,8-Hexahydro-7-methyl-3-[3-(4-(2-methoxyphenyl)-piperazin-1-yl)propyl]pyrido[4',3':4,5] thieno[2,3-d]pyrimidin-4-imine, m.p. 112–114° C.

16. 3,4,5,6,7,8-Hexahydro-7-benzyl-3-[3-(4-(2-methoxyphenyl)-piperazin-1-yl)propyl]pyrido[4',3':4,5] thieno[2,3-d]pyrimidin-4-imine×2 HCl, m.p. 258–261° C. (decomp.)

17. 3,4,5,6,7,8-Hexahydro-7-benzyl-3-[2-(4-phenylpiperazin-1-yl)-ethyl]pyrido[4',3':4,5]thieno[2,3-d]pyrimidin-4-imine, m.p. 168–170° C.

18. 3,4,5,6,7,8-Hexahydro-7-benzyl-3-[3-(4-(2-methoxyphenyl)-piperazin-1-yl)propyl]pyrido[4',3':4,5] thieno[2,3-d]-pyrimidin-4-one, m.p. 66–67° C.

19. 3,4,5,6,7,8-Hexahydro-7-benzyl-3-[2-(4-phenylpiperazin-1-yl)-ethyl]pyrido[4',3':4,5]thieno[2,3-d]pyrimidin-4-one, m.p. 70–71° C.

20. 3,4,5,6,7,8-Hexahydro-7-methyl-3-[2-(4-pyrimidin-2-yl-piperazin-1-yl)ethyl]pyrido[4',3':4,5]thieno[2,3-d]-pyrimidin-4-imine tritartrate, m.p. 112–114° C. (decomp.)

21. 3,4,5,6,7,8-Hexahydro-7-methyl-3-[3-(4-(3-methoxyphenyl)-piperazin-1-yl)propyl]pyrido[4',3':4,5] thieno[2,3-d]-pyrimidin-4-imine×3 HCl×2 H$_2$O, m.p. 268–270° C. (decomp.)

22. 3,4,5,6,7,8-Hexahydro-7-methyl-3-[3-(4-naphth-1-ylpiperazin-1-yl)propyl]pyrido[4',3':4,5]thieno[2,3-d] pyrimidin-4-imine×3 HCl, m.p. 250–253° C. (decomp.)

23. 3,4,5,6,7,8-Hexahydro-7-methyl-3-[3-(4-(2-nitrophenyl)piperazin-1-yl)propyl]pyrido[4',3':4,5]thieno [2,3-d]-pyrimidin-4-imine×3 HCl×2 H$_2$O, m.p. 271–273° C. (decomp.)

24. 3,4,5,6,7,8-Hexahydro-7-methyl-3-[3-(4-(2-methylphenyl)-piperazin-1-yl)propyl]pyrido[4',3':4,5] thieno[2,3-d]pyrimidin-4-imine×3 HCl, m.p. 280–282° C. (decomp.)

25. 3,4,5,6,7-Hexahydro-7-methyl-3-[3-(4-(2-aminophenyl)piperazin-1-yl)propyl]pyrido[4',3':4,5]thieno[2,3-d]-pyrimidin-4-imine×HCl×4 H₂O, m.p. 113–115° C. (decomp.)
26. 3,4,5,6,7,8-Hexahydro-7-methyl-3-[3-(4-(2-chlorophenyl)-piperazin-1-yl)propyl]pyrido[4',3':4,5]thieno[2,3-d]-pyrimidin-4-imine×3 HCl, m.p. 261–263° C. (decomp.)
27. 3,4,5,6,7,8-Hexahydro-7-methyl-3-[2-(4-pyrimidin-2-ylpiperazin-1-yl)ethyl]pyrido[4',3':4,5]thieno[2,3-d]-pyrimidin-4-one, m.p. 146–148° C.
28. 3,4,5,6,7,8-Hexahydro-7-methyl-3-[3-(4-benzylpiperidin-1-yl)propyl]pyrido[4',3':4,5]thieno[2,3-d]pyrimidin-4-imine×3 HCl, m.p. 295–297° C. (decomp.)
29. 3,4,5,6,7,8-Hexahydro-7-methyl-3-[3-(4-(2-hydroxyphenyl)-piperazin-1-yl)propyl]pyrido[4',3':4,5]thieno[2,3-d]-pyrimidin-4-imine, m.p. 164–166° C.
30. 3,4,5,6,7,8-Hexahydro-7-methyl-3-[4-(4-(2-methoxyphenyl)-piperazin-1-yl)butyl]pyrido[4',3':4,5]thieno[2,3-d]-pyrimidin-4-imine×HCl×3 H₂O, m.p. 272–274° C. (decomp.)
31. 3,4,5,6,7,8-Hexahydro-7-methyl-3-[3-(4-(2-ethoxyphenyl)-piperazin-1-yl)propyl]pyrido[4',3':4,5]thieno[2,3-d]-pyrimidin-4-imine×3 HCl×3 H₂O, m.p. 284–286° C. (decomp.)
32. 3,4,5,6,7,8-Hexahydro-7-methyl-3-[3-(4-(2-ethylphenyl)-piperazin-1-yl)propyl]pyrido[4',3':4,5]thieno[2,3-d]-pyrimidin-4-imine×3 HCl, m.p. 303–305° C. (decomp.)
33. 3,4,5,6,7,8-Hexahydro-7-methyl-3-[3-(4-(2-cyanophenyl)-piperazin-1-yl)propyl]pyrido[4',3':4,5]thieno[2,3-d]-pyrimidin-4-one×2 HCl×H₂O, m.p. 136–138° C. (decomp.)
34. 3,4,5,6,7,8-Hexahydro-7-methyl-3-[3-(4-phenylpiperidin-1-yl)propyl]pyrido[4',3':4,5]thieno[2,3-d]pyrimidin-4-imine×3 HCl, m.p. 280–282° C. (decomp.)
35. 3,4,5,6,7,8-Hexahydro-7-methyl-3-[3-(4-pyrazin-2-ylpiperazin-1-yl)propyl]pyrido[4',3':4,5]thieno[2,3-d]-pyrimidin-4-imine×4 HCl×H₂O, m.p. 284–286° C. (decomp.)
36. 3,4,5,6,7,8-Hexahydro-7-methyl-3-[3-(4-pyrimidin-2-yl-piperazin-1-yl)propyl]pyrido[4',3':4,5]thieno[2,3-d]-pyrimidin-4-imine, m.p. 161–163° C.
37. 3,4,5,6,7,8-Hexahydro-7-methyl-3-[3-(4-(2-cyanophenyl)-piperazin-1-yl)propyl]pyrido[4',3':4,5]thieno[2,3-d]pyrimidin-4-imine, m.p. 148–150° C.
38. 3,4,5,6,7,8-Hexahydro-7-benzyl-3-[2-(4-(2-methoxyphenyl)-piperazin-1-yl)ethyl]pyrido[4',3':4,5]thieno[2,3-d]-pyrimidin-4-one×3 HCl×H₂O, m.p. 288–290° C. (decomp.)
39. 3,4,5,6,7,8-Hexahydro-7-methyl-3-[3-(4-(3,4-methylenedioxy-phenyl)piperazin-1-yl)propyl]pyrido[4',3':4,5]thieno[2,3-d]-pyrimidin-4-imine×3 HCl, m.p. 288–290° C. (decomp.)
40. 3,4,5,6,7,8-Hexahydro-7-methyl-3-[2-(4-(2-methylphenyl)-piperazin-1-yl)ethyl]pyrido[4',3':4,5]thieno[2,3-d]-pyrimidin-4-one×2HCl×H₂O, m.p. >300° C.
41. 3,4,5,6,7,8-Hexahydro-7-methyl-3-[2-(4-(2-chlorophenyl)-piperazin-1-yl)-ethyl]pyrido[4',3':4,5]thieno[2,3-d]-pyrimidin-4-one×2HCl×H₂O, m.p. >300° C.
42. 3,4,5,6,7,8-Hexahydro-7-methyl-3-[2-(4-(3,4-dimethylphenyl)-piperazin-1-yl)ethyl]pyrido[4',3':4,5]thieno[2,3-d]pyrimidin-4-one×2HCl, m.p. 307–310° C.
43. 3,4,5,6,7,8-Hexahydro-7-methyl-3-[2-(4-(2,6-dimethylphenyl)-piperazin-1-yl)ethyl]pyrido[4',3':4,5]thieno[2,3-d]pyrimidin-4-one×2HCl, m.p. 297–300° C.
44. 3,4,5,6,7,8-Hexahydro-7-methyl-3-[2-(4-(2,3-dimethylphenyl)-piperazin-1-yl)ethyl]pyrido[4',3':4,5]thieno[2,3-d]pyrimidin-4-one, m.p. 163–167° C.
45. 3,4,5,6,7,8-Hexahydro-7-methyl-3-[2-(4-(2,4-dimethylphenyl)-piperazin-1-yl)ethyl]pyrido[4',3':4,5]thieno[2,3-d]pyrimidin-4-one×2HCl, m.p. 300–303° C.
46. 3,4,5,6,7,8-Hexahydro-7-methyl-3-[2-(4-(3,5-dichlorophenyl)-piperazin-1-yl)ethyl]pyrido[4',3':4,5]thieno[2,3-d]pyrimidin-4-one, m.p. 97–100° C.
47. 3,4,5,6,7,8-Hexahydro-7-methyl-3-[2-(4-(2,4-dimethoxyphenyl)-piperazin-1-yl)ethyl]pyrido[4',3':4,5]thieno-[2,3-d]pyrimidin-4-one×2HCl, m.p. 287–290° C.
48. 3,4,5,6,7,8-Hexahydro-7-methyl-3-[2-(4-(3-trifluoromethylphenyl)piperazin-1-yl)ethyl]pyrido[4',3':4,5]thieno[2,3-d]-pyrimidin-4-one×2HCl, m.p. 309–312° C.
49. 3,4,5,6,7,8-Hexahydro-7-methyl-3-[2-(4-naphth-1-ylpiperazin-1-yl)ethyl]pyrido[4',3':4,5]thieno[2,3-d]pyrimidin-4-one×2HCl×H₂O, m.p. 298–300° C. (decomp.)
50. 3,4,5,6,7,8-Hexahydro-7-methyl-3-[3-(4-(3-hydroxyphenyl)-piperazin-1-yl)propyl]pyrido[4',3':4,5]thieno[2,3-d]-pyrimidin-4-imine×2HCl×2H₂O, m.p. 182–184° C. (decomp.)
51. 3,4,5,6,7,8-Hexahydro-7-methyl-3-[2-(4-(2-methoxy-5-chlorophenyl)piperazin-1-yl)ethyl]pyrido[4',3':4,5]thieno-[2,3-d]pyrimidin-4-one×3HCl, m.p. 170–172° C. (decomp.)
52. 3,4,5,6,7,8-Hexahydro-7-methyl-3-[2-(4-(2,5-dimethoxyphenyl)-piperazin-1-yl)ethyl]pyrido[4',3':4,5]thieno-[2,3-d]pyrimidin-4-one×3HCl×H₂O, m.p. 176–178° C. (decomp.)
53. 3,4,5,6,7,8-Hexahydro-7-methyl-3-[2-(4-(2-methoxy-5-phenyl-phenyl)piperazin-1-yl)ethyl]pyrido[4',3':4,5]thieno-[2,3-d]pyrimidin-4-one×H₂O, m.p. 79–80° C.
54. 3,4,5,6,7,8-Hexahydro-7-methyl-3-[2-(4-(2-methoxyphenyl)3,4-dehydropiperidin-1-yl)ethyl]pyrido[4',3':4,5]thieno[2,3-d]-pyrimidin-4-one×2HCl×2H₂O, m.p. 182–185° C. (decomp.)
55. 3,4,5,6,7,8-Hexahydro-7-methyl-3-[2-(4-(2-hydroxyphenyl)-piperazin-1-yl)ethyl]pyrido[4',3':4,5]thieno[2,3-d]-pyrimidin-4-one×2HCl×H₂O, m.p. 281–283° C. (decomp.)
56. 3,4,5,6,7,8-Hexahydro-7-methyl-3-[2-(4-(7-methoxynaphth-1-yl)piperazin-1-yl)ethyl]pyrido[4',3':4,5]thieno-[2,3-d]pyrimidin-4-one×2HCl×H₂O, m.p. 272–274° C. (decomp.)
57. 3,4,5,6,7,8-Hexahydro-7-methyl-3-[2-(4-naphth-1-ylpiperazin-1-yl)ethyl]pyrido[4',3':4,5]thieno[2,3-d]pyrimidin-4-imine×3HCl, m.p. 288–289° C. (decomp.)
58. 3,4,5,6,7,8-Hexahydro-7-methyl-3-[2-(4-(4,5-methylenedioxybenzyl)piperazin-1-yl)ethyl]pyrido[4',3':4,5]thieno[2,3-d]-pyrimidin-4-imine×4HCl×2H₂O, m.p. 249–251° C. (decomp.)
59. 3,4,5,6,7,8-Hexahydro-7-methyl-3-[2-(4-(6-isopropylpyrimidin-4-yl)piperazin-1-yl)ethyl]pyrido[4',3':4,5]thieno[2,3-d]-pyrimidin-4-imine×3HCl×2H₂O, m.p. 250–253° C. (decomp)
60. 3,4,5,6,7,8-Hexahydro-7-methyl-3-[2-(4-(2-methoxynaphth-1-yl)piperazin-1-yl)ethyl]pyrido[4',3':4,5]thieno[2,3-d]-pyrimidin-4-one×2HCl×2H₂O, m.p. 241–243° C. (decomp.)
61. 3,4,5,6,7,8-Hexahydro-7-methyl-3-[2-(4-(2-methoxyphenyl)-piperazin-1-yl)ethyl]pyrido[4',3':4,5]thieno[2,3-d]-pyrimidin-4-one×2HCl×2H₂O, m.p. 299–301° C. (decomp.)
62. 3,4,5,6,7,8-Hexahydro-7-methyl-3-[2-(4-(3,4-dimethoxyphehyl)-piperazin-1-yl)ethyl]pyrido[4',3':4,5]thieno[2,3-d]-pyrimidin-4-one, m.p. 153–154° C.

63. 3,4,5,6,7,8-Hexahydro-7-methyl-3-[3-(4-naphth-1-ylpiperazin-1-yl)propyl]pyrido[4',3':4,5]thieno[2,3-d]pyrimidin-4-one×3HCl×2H$_2$O, m.p. 206–208° C. (decomp.)
64. 3,4,5,6,7,8-Hexahydro-7-methyl-3-[3-(4-pyrimidin-2-yl-piperazin-1-yl)propyl]pyrido[4',3':4,5]thieno[2,3-d]-pyrimidin-4-one, m.p. 161–163° C.
65. 3,4,5,6,7,8-Hexahydro-7-methyl-3-[2-(4-quinolin-2-yl-piperazin-1-yl)ethyl]pyrido[4',3':4,5]thieno[2,3-d]-pyrimidin-4-one, m.p. 143–145° C.
66. 3,4,5,6,7,8-Hexahydro-7-methyl-3-[2-(4-(2-methylnaphth-1-yl)-piperazin-1-yl-ethyl]pyrido[4',3':4,5]thieno[2,3-d]-pyrimidin-4-one×2HCl×2H$_2$O, m.p. 295–297° C. (decomp.)
67. 3,4,5,6,7,8-Hexahydro-7-methyl-3-[2-(4-(2-methoxy-3,5-di-chlorophenyl)piperazin-1-yl)ethyl]pyrido[4',3':4,5]-thieno[2,3-d]-pyrimidin-4-one×2HCl×H$_2$O, m.p. 264–267° C. (decomp.)
68. 3,4,5,6,7,8-Hexahydro-7-methyl-3-[2-(4-(2-cyanophenyl)-piperazin-1-yl)ethyl]pyrido[4',3':4,5]thieno[2,3-d]-pyrimidin-4-one, m.p. 162–164° C.
69. 3,4,5,6,7,8-Hexahydro-7-methyl-3-[2-(4-(2-chlorphenyl)-piperazin-1-yl)ethyl]pyrido[4',3':4,5]thieno[2,3-d]-pyrimidin-4-one, m.p. 165–167° C.
70. 3,4,5,6,7,8-Hexahydro-7-methyl-3-[2-(4-pyridin-2-ylpiperazin-1-yl)ethyl]pyrido[4',3':4,5]thieno[2,3-d]-pyrimidin-4-one×3HCl×2H$_2$O, m.p. 232–234° C. (decomp.)
71. 3,4,5,6,7,8-Hexahydro-7-methyl-3-[2-(4-pyridin-4-ylpiperazin-1-yl)ethyl]pyrido[4',3':4,5]thieno[2,3-d]-pyrimidin-4-one×3HCl×2H$_2$O, m.p. 270–272° C. (decomp.)
72. 3,4,5,6,7,8-Hexahydro-7-methyl-3-[2-(4-(5-methoxypyrimidin-4-yl)piperazin-1-yl)ethyl]pyrido[4',3':4,5]thieno[2,3-d]-pyrimidin-4-one×3HCl×4H$_2$O, m.p. 266–268° C. (decomp.)
73. 3,4,5,6,7,8-Hexahydro-7-methyl-3-[2-(4-naphth-2-ylpiperazin-1-yl)ethyl]pyrido[4',3':4,5]thieno[2,3-d]pyrimidin-4-one, m.p. 140–141° C.
74. 3,4,5,6,7,8-Hexahydro-7-methyl-3-[2-(4-pyrazin-2-ylpiperazin-1-yl)ethyl]pyrido[4',3':4,5]thieno[2,3-d]-pyrimidin-4-one×3HCl×3H$_2$O, m.p. 170–172° C. (decomp.)
75. 3,4,5,6,7,8-Hexahydro-7-methyl-3-[2-(4-tetralin-5-yl-piperazin-1-yl)ethyl]pyrido[4',3':4,5]thieno[2,3-d]-pyrimidin-4-one×3HCl×2H$_2$O, m.p. 285–287° C. (decomp.)
76. 3,4,5,6,7,8-Hexahydro-7-methyl-3-[2-(4-indan-1-ylpiperazin-1-yl)ethyl]pyrido[4',3':4,5]thieno[2,3-d]pyrimidin-4-one×HCl×2H$_2$O, m.p. 300–301° C. (decomp.)
77. 3,4,5,6,7,8-Hexahydro-7-methyl-3-[2-(4-(2-methoxy-4-nitro-5-methylphenyl)piperazin-1-yl)ethyl]pyrido[4',3':4,5]-thieno[2,3-d]pyrimidin-4-one×2HCl×2H$_2$O, m.p. 210–212° C. (decomp.)
78. 3,4,5,6,7,8-Hexahydro-7-methyl-3-[2-(4-isochinolin-4-yl-piperazin-1-yl)ethyl]pyrido[4',3':4,5]thieno[2,3-d]-pyrimidin-4-one×3HCl×3H$_2$O, m.p. 290–292° C. (decomp.)
79. 3,4,5,6,7,8-Hexahydro-7-methyl-3-[2-(4-(2-methoxy-4-chloro-5-methylphenyl)piperazin-1-yl)ethyl]pyrido[4',3':4,5]thieno-[2,3-d]pyrimidin-4-one×2HCl×2H$_2$O, m.p. 293–294° C. (decomp.)
80. 3,4,5,6,7,8-Hexahydro-7-methyl-3-[2-(4-(2,4-dimethoxyphenyl)-piperazin-1-yl)ethyl]pyrido[4',3':4,5]thieno-[2,3-d]pyrimidin-4-one×3HCl×3H$_2$O, m.p. 290–291° C. (decomp.)
81. 3,4,5,6,7,8-Hexahydro-7-methyl-3-[2-(4-quinazolin-4-yl-piperazin-1-yl)ethyl]pyrido[4',3':4,5]thieno[2,3-d]-pyrimidin-4-one×3HCl×4H$_2$O, m.p. 258–260° C. (decomp.)
82. 3,4,5,6,7,8-Hexahydro-7-methyl-3-[2-(4-(3-trifluoromethyl-4-chlorophenyl)piperazin-1-yl)ethyl]pyrido[4',3':4,5]thieno-[2,3-d]pyrimidin-4-one×2HCl×3H$_2$O, m.p. 311–312° C. (decomnp.)
83. 3,4,5,6,7,8-Hexahydro-7-(4-chlorobenzyl)-3-[2-(4-(2-methoxyphenyl)piperazin-1-yl)ethyl]pyrido[4',3':4,5]thieno-[2,3-d]pyrimidin-4-one×3HCl×H$_2$O, m.p. 290–292° C. (decomp.)
84. 3,4,5,6,7,8-Hexahydro-7-ethyl-3-[2-(4-(2-methoxyphenyl)-piperazin-1-yl)ethyl]pyrido[4',3':4,5]thieno[2,3-d]-pyrimidin-4-one×3HCl×H$_2$O, m.p. 295–297° C. (decomp.)
85. 3,4,5,6,7,8-Hexahydro-7-isopropyl-3-[2-(4-(2-methoxyphenyl)-piperazin-1-yl)ethyl]pyrido[4',3':4,5]thieno-[2,3-d]pyrimidin-4-one×3HCl×H$_2$O, m.p. 300–302° C. (decomp.)
86. 3,4,5,6,7,8-Hexahydro-7-(4-nitro)benzyl-3-[2-(4-(2-methoxyphenyl)piperazin-1-yl)ethyl]pyrido[4',3':4,5]thieno[2,3-d]-pyrimidin-4-one×3HCl×H$_2$O, m.p. 214–217° C. (decomp.)
87. 3,4,5,6,7,8-Hexahydro-7-(4-methoxy)benzyl-3-[2-(4-(2-methoxyphenyl)piperazin-1-yl)ethyl]pyrido[4',3':4,5]-thieno[2,3-d]pyrimidin-4-one×3HCl×H$_2$O, m.p. 278–281° C. (decomp.)
88. 3,4,5,6,7,8-rHexahydro-7-(2-phenyl)ethyl-3-[2-(4-(2-methoxyphenyl)piperazin-1-yl)ethyl]pyrido[4',3':4,5]thieno-[2,3-d]pyrimidin-4-one×3HCl×H$_2$O, m.p. 305–306° C. (decomp.)
89. 3,4,5,6,7,8-Hexahydro-7-(3-benzoyl)propyl-3-[2-(4-(2-methoxyphenyl)piperazin-1-yl)ethyl]pyrido[4',3':4,5]-thieno[2,3-d]pyrimidin-4-one×3HCl×H$_2$O, m.p. 124–126° C. (decomp.)
90. 3,4,5,6,7,8-Hexahydro-7-(4-amino)benzyl-3-[2-(4-(2-methoxyphenyl)piperazin-1-yl)ethyl]pyrido[4',3':4,5]thieno-[2,3-d]pyrimidin-4-one×HCl×3H$_2$O, m.p. 280–282° C. (decomp.)
91. 3,4,5,6,7,8-Hexahydro-7-(3-phenyl)propyl-3-[2-(4-(2-methoxyphenyl)piperazin-1-yl)ethyl]pyrido[4',3':4,5]-thieno[2,3-d]pyrimidin-4-one×2HCl×3H$_2$O, m.p. 301–302° C. (decomp.)
92. 3,4,5,6,7,8-Hexahydro-7-(3-phenyl)propyl-3-[2-(4-naphth-1-yl)piperazin-1-yl)ethyl]pyrido[4',3':4,5]thieno[2,3-d]-pyrimidin-4-one×2HCl×2H$_2$O, m.p. 306–307° C. (decomp.)
93. 3,4,5,6,7,8-Hexahydro-7-(2-(4-methoxy)phenyl)ethyl-3-[2-(4-naphth-1-yl)piperazin-1-yl)ethyl]pyrido[4',3':4,5]thieno-[2,3-d]pyrimidin-4-one×2HCl×3H$_2$O, m.p. 306–308° C. (decomp.)
94. 3,4,5,6,7,8-Hexahydro-7-(2-(4-chloro)phenyl)ethyl-3-[2-(4-naphth-1-yl)piperazin-1-yl)ethyl]pyrido[4',3':4,5]thieno-[2,3-d]pyrimidin-4-one×2HCl×3H$_2$O, m.p. 300–303° C. (decomp.)
95. 3,4,5,6,7,8-Hexahydro-7-(2-phenyl)ethyl-3-[2-(4-naphth-1-yl)-piperazin-1-yl)ethyl]pyrido[4',3':4,5]thieno[2,3-d]pyrimidin-4-one×2HCl×3H$_2$O, m.p. 295–298° C.
96. 3,4,5,6,7,8-Hexahydro-7-(2-(4-hydroxy)phenyl)ethyl-3-[2-(4-naphth-1-yl)piperazin-1-yl)ethyl]pyrido[4',3':4,5]thieno-[2,3-d]pyrimidin-4-one×2HCl×2H$_2$O, m.p. 254–256° C.
97. 3,4,5,6,7,8-Hexahydro-7-(2-(4-chloro)phenyl)ethyl-3-[2-(4-(2-methoxyphenyl)piperazin-1-yl)ethyl]pyrido[4',3':4,5]-thieno[2,3-d]pyrimidin-4-one×3HCl×2H$_2$O, m.p. 304–306° C. (decomp.)

98. 3,4,5,6,7,8-Hexahydro-7-(2-naphth-1-yl)ethyl-3-[2-(4-(2-methoxyphenyl)piperazin-1-yl)ethyl]pyrido[4',3':4,5]-thieno[2,3-d]pyrimidin-4-one×2HCl×2H₂O, m.p. 293–295° C. (decomp.)
99. 3,4,5,6,7,8-Hexahydro-7-(2-benzoylamino)ethyl-3-[2-(4-naphth-1-yl)piperazin-1-yl)ethyl]pyrido[4',3':4,5]-thieno[2,3-d]-pyrimidin-4-one×2HCl×2H₂O, m.p. 292–294° C. (decomp.)
100. 3,4,5,6,7,8-Hexahydro-7-(2-benzoylamino)ethyl-3-[2-(4-(2-methoxyphenyl)piperazin-1-yl)ethyl]pyrido[4',3':4,5]-thieno[2,3-d]pyrimidin-4-one×2HCl×3H₂O, m.p. 202–204° C. (decomp.)
101. 3,4,5,6,7,8-Hexahydro-7-(3-benzoylamino)propyl-3-[2-(4-(2-methoxyphenyl)piperazin-1-yl)ethyl]pyrido[4',3':4,5]-thieno[2,3-d]pyrimidin-4-one×3HCl×2H₂O, m.p. 182–183° C. (decomp.)
102. 3,4,5,6,7,8-Hexahydro-7-(3-benzoylamino)propyl-3-[2-(4-naphth-1-yl)piperazin-1-yl)ethyl]pyrido[4',3':4,5]thieno-[2,3-d]pyrimidin-4-one×3HCl×H₂O, m.p. 128–130° C.
103. 3,4,5,6,7,8-Hexahydro-7-(4-phenyl)butyl-3-[2-(4-(2-methoxyphenyl)piperazin-1-yl)ethyl]pyrido[4',3':4,5]thieno-[2,3-d]pyrimidin-4-one×3HCl×H₂O, m.p. 311–312° C. (decomp.)
104. 3,4,5,6,7,8-Hexahydro-7-(4-phenyl)butyl-3-[2-(4-naphth-1-yl)-piperazin-1-yl)ethyl]pyrido[4',3':4,5]thieno[2,3-d]-pyrimidin-4-one×3HCl×H₂O, m.p. 312–314° C. (decomp.)
105. 3,4,5,6,7,8-Hexahydro-7-(4-methoxy)benzyl-3-[2-(4-naphth-1-yl)piperazin-1-yl)ethyl]pyrido[4',3':4,5]thieno[2,3-d]pyrimidin-4-one×3HCl×H₂O, m.p. 275–277° C. (decomp.)
106. 3,4,5,6,7,8-Hexahydro-7-(2-(4-methoxy)phenyl)ethyl-3-[2-(4-(2-methoxyphenyl)piperazin-1-yl)ethyl]pyrido-[4',3':4,5]thieno[2,3-d]pyrimidin-4-one×3HCl×3H₂O, m.p. 297–298° C. (decomp.)
107. 3,4,5,6,7,8-Hexahydro-7-(2-phenyl)ethyl-3-[3-(4-naphth-1-yl)-piperazin-1-yl)propyl]pyrido[4',3':4,5]thieno[2,3-d]pyrimidin-4-one, m.p. 153–155° C.
108. 3,4,5,6,7,8-Hexahydro-7-(2-phenyl)ethyl-3-[2-(4-pyrimidin-2-yl)piperazin-1-yl)ethyl)pyrido[4',3':4,5]thieno[2,3-d]pyrimidin-4-one×2HCl×3H₂O, m.p. 304–305° C. (decomp.)
109. 3,4,5,6,7,8-Hexahydro-7-(2-phenyl)ethyl-3-[3-(4-pyrimidin-2-yl)piperazin-1-yl)propyl)pyrido[4',3':4,5]thieno[2,3-d]-pyrimidin-4-one×3HCl×2H₂O, m.p. 302–303° C. (decomp.)
110. 3,4,5,6,7,8-Hexahydro-7-(3-benzoylamino)propyl-3-[2-(4-pyrimidin-2-yl)piperazin-1-yl)ethyl]pyrido[4',3':4,5]-thieno[2,3-d]pyrimidin-4-one×3HCl×3H₂O, m.p. 125–127° C. (decomp.)
111. 3,4,5,6,7,8-Hexahydro-7-(4-phenyl)butyl-3-[2-(4-pyrimidin-2-yl)piperazin-1-yl)ethyl)pyrido[4',3':4,5]thieno[2,3-d]-pyrimidin-4-one×3HCl×3H₂O, m.p. 317–319° C. (decomp.)
112. 3,4,5,6,7,8-Hexahydro-7-(2-(4-methoxy)phenyl)ethyl-3-[2-(4-pyrimidin-2-yl)piperazin-1-yl)ethylpyrido[4',3':4,5]thieno-[2,3-d]-pyrimidin-4-one, m.p. 165–167° C.
113. 3,4,5,6,7,8-Hexahydro-7-acetyl-3-[3-(4-(2-methoxyphenyl)-piperazin-1-yl)propyl]pyrido[4',3':4,5]thieno[2,3-d]-pyrimidin-4-imine×2HCl, m.p. 265–268° C.
114. 3,4,5,6,7,8-Hexahydro-7-acetyl-3-[3-(4-(2-methoxyphenyl)-piperazin-1-yl)propyl]pyrido[4',3':4,5]thieno[2,3-d]-pyrimidin-4-one×2HCl×2H₂O, m.p. 264–267° C.
115. 3,4,5,6,7,8-Hexahydro-3-[2-(4-(2-methoxyphenyl)-piperazin-1-yl)ethyl]pyrido[4',3':4,5]thieno[2,3-d]pyrimidin-4-one, m.p. 168–170° C.
116. 3,4,5,6,7,8-Hexahydro-7-acetyl-3-[2-(4-(2-methoxyphenyl)-piperazin-1-yl)ethyl]pyrido[4',3':4,5]thieno[2,3-d]-pyrimidin-4-one, m.p. 170–172° C.
117. 3,4,5,6,7,8-Hexahydro-7-benzoyl-3-[2-(4-(2-methoxyphenyl)-piperazin-1-yl)ethyl]pyrido[4',3':4,5]thieno[2,3-d]-pyrimidin-4-one×2HCl×2H₂O, m.p. 185–187° C. (decomp.)
118. 3,4,5,6,7,8-Hexahydro-7-benzoyl-3-[2-(4-naphth-1-yl)-piperazin-1-yl)ethyl]pyrido[4',3':4,5]thieno[2,3-d]-pyrimidin-4-one, m.p. 195–197° C.
119. 3,4,5,6,7,8-Hexahydro-7-benzoyl-3-[2-(4-pyrimidin-2-yl)-piperazin-1-yl)ethyl]pyrido[4',3':4,5]thieno[2,3-d]-pyrimidin-4-one, m.p. 130–132° C. (decomp.)
120. 3,4,5,6,7,8-Hexahydro-2,7-dimethyl-3-[2-(4-(2-methoxyphenyl)-piperazin-1-yl)ethyl]pyrido[4',3':4,5]thieno-[2,3-d]-pyrimidin-4-one, m.p. 176–178° C.
121. 3,4,5,6,7,8-Hexahydro-7-acetyl-2-hydroxy-3-[2-(4-(2-methoxyphenyl)piperazin-1-yl)ethyl]pyrido[4',3':4,5]thieno-[2,3-d]pyrimidin-4-one, m.p. 135–137° C.
122. 3,4,5,6,7,8-Hexahydro-7-methyl-3-[1-(4-(2-methoxyphenyl)-piperazin-1-yl)prop-2-yl]pyrido[4',3':4,5]thieno[2,3-d]-pyrimidin-4-one, m.p. 184–186° C.
123. 3,4,5,6,7,8-Hexahydro-3-[1-(4-naphth-1-ylpiperazin-1-yl)prop-2-yl]pyrido[4',3':4,5]thieno[2,3-d]pyrimidin-4-one×2HCl×4H₂O, m.p. 242–244° C. (decomp.)
124. 3,4,5,6,7,8-Hexahydro-7-methyl-3-[2-(4-(2-methoxyphenyl)-piperazin-1-yl)propyl]pyrido[4',3':4,5]thieno[2,3-d]-pyrimidin-4-one×3HCl×3H₂O, m.p. 190–192° C. (decomp.)
125. 3,4,5,6,7,8-Hexahydro-7-methyl-3-[2-(4-(isoquinolin-1-yl)-piperazin-1-yl)ethyl]pyrido[4',3':4,5]thieno[2,3-d]-pyrimidin-4-one×3HCl×3H₂O, m.p. >250° C.
126. 3,4,5,6,7,8-Hexahydro-7-methyl-3-[2-(4-(6-methylpyridin-2-yl)piperazin-1-yl)ethyl]pyrido[4',3':4,5]thieno[2,3-d]pyrimidin-4-one, m.p. 138–140° C.
127. 3,4,5,6,7,8-Hexahydro-7-methyl-3-[2-(4-(4-trifluoromethyl-pyrimidin-2-yl)piperazin-1-yl)ethyl]pyrido[4',3':4,5]-thieno[2,3-d]pyrimidin-4-one, m.p. 291–292° C.
128. 3,4,5,6,7,8-Hexahydro-7-methyl-3-[2-(4-(3-trifluoromethylphenyl)-3,4-dehydropiperidin-1-yl)ethyl]pyrido[4',3':4,5]-thieno[2,3-d]pyrimidin-4-one, m.p. 98–100° C.
129. 3,4,5,6,7,8-Hexahydro-7-methyl-3-[2-(4-(3,4-dimethoxyphenyl)piperazin-1-yl)ethyl]pyrido[4',3':4,5]thieno[2,3-d]-pyrimidin-4-one×2HCl×2H₂O, m.p. 212–214° C.
130. 3,4,5,6,7,8-Hexahydro-7-methyl-3-[2-(4-(3-methoxyphenyl)-piperazin-1-yl)ethyl]pyrido[4',3':4,5]thieno[2,3-d]-pyrimidin-4-one, ¹H NMR (CDCl₃) δ=2.5 (3H, s), 3.8 (3H, s), 7.9 (1H, s)
131. 3,4,5,6,7,8-Hexahydro-7-methyl-3-[2-(4-(3,5-dimethoxyphenyl]piperazin-1-yl)ethyl]pyrido[4',3':4,5]thieno-[2,3-d]pyrimidin-4-one, ¹H NMR (CDCl₃ δ=2.5 (3H, s), 3.8 (6H, s), 6.1 (2H), 7.9 (1H, s)
132. 3,4,5,6,7,8-Hexahydro-7-methyl-3-[5-(4-(3-trifluoromethyl-4-chlorophenyl))piperazin-1-yl)pentyl]pyrido[4',3':4,5]-thieno-[2,3-d]pyrimidin-4-one, ¹H NMR (DMSO-d₆) δ=2.5 (3H, s), 7.2 (1H, d), 8.5 (1H, s)
132. 3,4,5,6,7,8-Hexahydro-7-methyl-3-[5-(4-(3-trifluoromethyl-4-chlorophenyl)piperrazin-1-yl)pentyl]pyrido[4',3':4,5]thieno-[2,3-d]pyrimidin-4-one, ¹H NMR (DMSO-d₆) δ=2.5 (3H, s), 7.2 (1H, d), 8.5 (1H, s)
133. 3,4,5,6,7,8-Hexahydro-7-methyl-3-[4-(4-naphth-1-yl-piperazin-1-yl)butyl]pyrido[4',3':4,5]thieno[2,3-d]-pyrimidin-4-one, ¹H NMR (CDCl₃) δ=2.5 (3H, s), 4.0 (2H, t), 7.1 (1H, d), 7.9 (1H, s)

134. 3,4,5,6,7,8-Hexahydro-7-methyl-3-[4-(4-pyridin-2-yl-piperazin-1-yl)butyl]pyrido[4',3':4,5]thieno[2,3-d]-pyrimidin-4-one, $^1$H NMR (CDCl$_3$) δ=2.8 (2H, t), 3.6 (2H, s), 4.0 (2H, t), 7.9 (1H, s)

135. 3,4,5,6,7,8-Hexahydro-7-methyl-3-[4-(4-(6-methylpyridin-2-yl)piperazin-1-yl)butyl]pyrido[4',3':4,5]thieno[2,3-d]-pyrimidin-4-one, $^1$H NMR (DMSO-d$_6$) δ=2.5 (3H, s), 6.8 (1H, d), 8.5 (1H, s)

136. 3,4,5,6,7,8-Hexahydro-7-methyl-3-[4-(4-pyrimidin-2-yl-piperazin-1-yl)butyl]pyrido[4',3':4,5]thieno[2,3-d]-pyrimidin-4-one, $^1$H NMR (DMSO-d$_6$) δ=2.5 (3H, s), 8.4 (1H, d), 8.5 (1H, s)

137. 3,4,5,6,7,8-Hexahydro-7-methyl-3-[4-(4-phenyl-3,4-dehydropiperidin-1-yl)butyl]pyrido[4',3':4,5]thieno[2,3-d]-pyrimidin-4-one, $^1$H NMR (CDCl$_3$) δ=2.5 (3H, s), 3.6 (2H, s), 7.9 (1H, s)

138. 3,4,5,6,7,8-Hexahydro-7-methyl-3-[2-(4-(4-methylnaphth-1-yl)piperazin-1-yl)ethyl]pyrido[4',3':4,5]thieno[2,3-d]-pyrimidin-4-one, m.p. 139–141° C.

139. 3,4,5,6,7,8-Hexahydro-7-methyl-3-[2-(4-(3-trifluoromethylphenyl)piperidin-1-yl)ethyl]pyrido[4',3':4,5]thieno-[2,3-d]pyrimidin-4-one×2HCl×H$_2$O, m.p. 290–295° C.

140. 3,4,5,6,7,8-Hexahydro-7-methyl-3-[2-(4-(4-fluoronaphth-1-yl)-piperazin-1-yl)ethyl]pyrido[4',3':4,5]thieno[2,3-d]-pyrimidin-4-one, m.p. 157–158° C.

141. 3,4,5,6,7,8-Hexahydro-7-methyl-3-[2-(4-(4-trifluoromethylpyridin-2-yl)piperazin-1-yl)ethyl]pyrido[4',3':4,5]thieno-[2,3-d]pyrimidin-4-one, m.p. 101–102° C.

142. 3,4,5,6,7,8-Hexahydro-7-methyl-3-[2-(4-pyridin-2-yl-piperazin-1-yl)ethyl]pyrido[4',3':4,5]thieno[2,3-d]-pyrimidin-4-one×HCl, $^1$H NMR (D$_2$O) δ=3.1 (3H, s), 4.4 (2H, t), 7.0 (1H, t), 8.4 (1H, s)

143. 3,4,5,6,7,8-Hexahydro-7-methyl-3-[4-(4-phenylpiperidin-1-yl)butyl]pyrido[4',3':4,5]thieno[2,3-d]pyrimidin-4-one, $^1$H NMR (CDCl$_3$) δ=2.5 (3H, s), 4.0 (2H, t), 7.9 (1H, s)

144. 3,4,5,6,7,8-Hexahydro-7-methyl-3-[2-(4-(3-trifluoromethylpyridin-2-yl)piperazin-1-yl)ethyl]pyrido[4',3':4,5]thieno-[2,3-d]pyrimidin-4-one, m.p. 124–125° C.

145. 3,4,5,6,7,8-Hexahydro-7-methyl-3-[2-(4-phenylpiperazin-1-yl)ethyl]pyrido[4',3':4,5]thieno[2,3-d]pyrimidin-4-one, m.p. 121–123° C.

146. 3,4,5,6,7,8-Hexahydro-7-isopropyl-3-[2-(4-(3-trifluoromethylphenylpiperazin-1-yl)ethyl]pyrido[4',3':4,5]thieno-[2,3-d]pyrimidin-4-one×2HCl×H$_2$O, m.p. 225–227° C.

147. 3,4,5,6,7,8-Hexahydro-7-methyl-3-[2-(4-(4-trifluoromethyl-6-methylpyridin-2-yl)piperazin-1-yl)ethyl]pyrido-[4',3':4,5]thieno[2,3-d]pyrimidin-4-one×3HCl×2H$_2$O, m.p. 280–282° C.

148. 3,4,5,6,7,8-Hexahydro-7-methyl-3-[2-(4-(3-cyanophenylpiperazin-1-yl)ethyl]pyrido[4',3':4,5]thieno(2,3-d]-pyrimidin-4-one×2HCl, m.p. 268–270° C.

149. 3,4,5,6,7,8-Hexahydro-7-methyl-3-[2-(4-(6-trifluoromethylpyridin-2-yl)piperazin-1-yl)ethyl]pyrido[4',3':4,5]thieno-[2,3-d]pyrimidin-4-one×2HCl, m.p. 290–292° C.

150. 3,4,5,6,7,8-Hexahydro-7-methyl-3-[2-(4-(6-methylpyridin-2-yl)homopiperazin-1-yl)ethyl]pyrido[4',3':4,5]thieno-[2,3-d]pyrimidin-4-one×3HCl×H$_2$O, m.p. 212–214° C.

151. 3,4,5,6,7,8-Hexahydro-7-methyl-3-[2-(4-phenylhomopiperazin-1-yl)ethyl]pyrido[4',3':4,5]thieno[2,3-d]pyrimidin-4-one×3HCl×H$_2$O, m.p. 222–223° C.

152. 3,4,5,6,7,8-Hexahydro-7-methyl-3-[2-(4-(3-trifluoromethylphenyl)homopiperazin-1-yl)ethyl]pyrido[4',3':4,5]-thieno[2,3-d]pyrimidin-4-one×2HCl×H$_2$O, m.p. >280° C.

153. 3,4,5,6,7,8-Hexahydro-7-methyl-3-[2-(4-(4-methylpyrimidin-2-yl)piperazin-1-yl)ethyl]pyrido[4',3':4,5]thieno[2,3-d]-pyrimidin-4-one, m.p. 136–138° C.

154. 3,4,5,6,7,8-Hexahydro-7-methyl-3-[4-(4-phenylpiperidin-1-yl)butyl]pyrido[4',3':4,5]thieno[2,3-d]pyrimidin-4-one, ESI MS: [M+H]$^+$=437

155. 3,4,5,6,7,8-Hexahydro-7-methyl-3-[2-(4-(3-phenoxyphenyl)-piperazin-1-yl)ethyl]pyrido[4',3':4,5]thieno[2,3-d]-pyrimidin-4-one, ESI MS: [M+H]$^+$=503

156. 3,4,5,6,7,8-Hexahydro-7-ethyl-3-[2-(4-(6-methylpyridin-2-yl)piperazin-1-yl)ethyl]pyrido[4',3':4,5]thieno-[2,3-d]pyrimidin-4-one, ESI MS: [M+H]$^+$=439

157. 3,4,5,6,7,8-Hexahydro-7-(2-(3-chloro-N-benzoyl)aminoethyl)-3-[2-(4-(6-methylpyridin-2-yl)piperazin-1-yl)ethyl]-pyrido[4',3':4,5]thieno[2,3-d]pyrimidin-4-one, ESI MS: [M]$^+$=592

158. 3,4,5,6,7,8-Hexahydro-7-(2-nicotinamidoethyl)-3-[2-(4-(3-trifluoromethylphenyl)piperazin-1-yl)ethyl]pyrido-[4',3':4,5]thieno[2,3-d]pyrimidin-4-one, ESI MS: [M+H]$^+$=612

159. 3,4,5,6,7,8-Hexahydro-7-(2-(4-chloro-N-benzoyl)aminoethyl)-3-[2-(4-(6-methylpyridin-2-yl)piperazin-1-yl)ethyl]-pyrido[4',3':4,5]thieno[2,3-d]pyrimidin-4-one, ESI MS: [M+2H]$^+$=594

160. 3,4,5,6,7,8-Hexahydro-7-methyl-3-[4-(4-(3-trifluoromethylphenyl)piperazin-1-yl)butyl]pyrido[4',3':4,5]thieno-[2,3-d]pyrimidin-4-one×2HCl, ESI MS: [M+H]$^+$=520

161. 3,4,5,6,7,8-Hexahydro-7-(2-(4-fluoro-N-benzoyl)aminoethyl)-3-[2-(4-(6-methylpyridin-2-yl)piperazin-1-yl)ethyl]-pyrido[4',3':4,5]thieno[2,3-d]pyrimidin-4-one, $^1$H NMR (270 MHz, CDCl$_3$): 2.4 (s, 3H), 2.6 (t, 4H), 4.1 (t, 2H), 6.4 (d, 1H), 6.5 (d, 1H), 6.8 (br, 1H), 7.1 (t, 2H), 7.4 (t, 1H), 7.8 (m, 1H), 8.0 (s, 1H)

162. 3,4,5,6,7,8-Hexahydro-7-propyl-3-[2-(4-(3-trifluoromethylphenyl)piperazin-1-yl)ethyl]pyrido[4',3':4,5]thieno-[2,3-d]pyrimidin-4-one×2HCl, ESI MS: [M+H]$^+$=506

163. 3,4,5,6,7,8-Hexahydro-7-(4-chlorobenzyl)-3-[2-(4-(6-methylpyridin-2-yl)piperazin-1-yl)ethyl]pyrido[4',3':4,5]-thieno[2,3-d]pyrimidin-4-one, ESI MS: [M]$^+$=535

164. 3,4,5,6,7,8-Hexahydro-3-[2-(4-(6-methylpyridin-2-yl)-piperazin-1-yl)ethyl]pyrido[4',3':4,5]thieno[2,3-d]-pyrimidin-4-one, ESI MS; [M+H]$^+$=411

165. 3,4,5,6,7,8-Hexahydro-7-acetyl-3-[2-(4-(6-methylpyridin-2-yl)piperazin-1-yl)ethyl]pyrido[4',3':4,5]thieno-[2,3-d]pyrimidin-4-one, ESI MS: [M+H]$^+$=453

166. 3,4,5,6,7,8-Hexahydro-7-methyl-3-[2-(4-(3-aminophenyl)-piperazin-1-yl)ethyl]pyrido[4',3':4,5]thieno[2,3-d]-pyrimidin-4-one×HCl, ESI MS: [M+H]$^+$=425

167. 3,4,5,6,7,8-Hexahydro-7-(4-fluorobenzyl)-3-[2-(4-(3-trifluoromethylphenyl)piperazin-1-yl)ethyl]pyrido-[4',3':4,5]thieno[2,3-d]pyrimidin-4-one, ESI MS: [M+H]$^+$=572

168. 3,4,5,6,7,8-Hexahydro-7-(2-(4-nitro-N-benzoyl)aminoethyl)-3-[2-(4-(3-trifluoromethylphenyl)piperazin-1-yl)ethyl]-pyrido[4',3':4,5]thieno[2,3-d]pyrimidin-4-one, ESI MS: [M+H]$^+$=656

169. 3,4,5,6,7,8-Hexahydro-7-isopropyl-3-[2-(4-(6-methylpyridin-2-yl)piperazin-1-yl)ethyl]pyrido[4',3':4,5]-thieno[2,3-d]pyrimidin-4-one, ESI MS: [M+H]$^+$=453

170. 3,4,5,6,7,8-Hexahydro-7-(2-methylpropyl)-3-[2-(4-(3-trifluoromethylphenyl)piperazin-1-yl)ethyl]pyrido-[4',3':4,5]thieno[2,3-d]pyrimidin-4-one, ESI MS: [M+H]$^+$=520

171. 3,4,5,6,7,8-Hexahydro-7-(2-methylpropyl)-3-[2-(4-(6-methylpyridin-2-yl)piperazin-1-yl)ethyl]pyrido-[4',3':4,5]thieno[2,3-d]pyrimidin-4-one, ESI MS: [M+H]$^+$=467

172. 3,4,5,6,7,8-Hexahydro-7-propyl-3-[2-(4-(6-methylpyridin-2-yl)piperazin-1-yl)ethyl]pyrido[4',3':4,5]thieno-[2,3-d]pyrimidin-4-one, ESI MS: [M+H]$^+$=453

173. 3,4,5,6,7,8-Hexahydro-7-(2-nicotinamidoethyl)-3-[2-(4-(6-methylpyridin-2-yl)piperazin-1-yl)ethyl]pyrido-[4',3':4,5]thieno[2,3-d]pyrimidin-4-one, ESI MS: [M+H]$^+$=559

174. 3,4,5,6,7,8-Hexahydro-7-(2-isonicotinamidoethyl)-3-[2-(4-(3-trifluoromethylphenyl)piperazin-1-yl)ethyl]pyrido-[4',3':4,5]thieno[2,3-d]pyrimidin-4-one, fumaric acid salt, ESI MS: [M+H]$^+$=608

175. 3,4,5,6,7,8-Hexahydro-7-cyclopropyl-3-[2-(4-(3-trifluoromethylphenyl)piperazin-1-yl)ethyl]pyrido[4',3':4,5]-thieno[2,3-d]pyrimidin-4-one, ESI MS: [M+H]$^+$=504

176. 3,4,5,6,7,8-Hexahydro-7-(2-phenoxyethyl)-3-[2-(4-(3-trifluoromethylphenyl)piperazin-1-yl)ethyl]pyrido-[4',3':4,5]thieno[2,3-d]pyrimidin-4-one×HCl, ESI MS: [M+H]$^+$=598

177. 3,4,5,6,7,8-Hexahydro-7-(2-benzyloxyethyl)-3-[2-(4-(6-methylpyridin-2-yl)piperazin-1-yl)ethyl]pyrido-[4',3':4,5]thieno[2,3-d]pyrimidin-4-one, ESI MS: [M+H]$^+$=545

178. 3,4,5,6,7,8-Hexahydro-7-cyclopropyl-3-[2-(4-(6-methylpyridin-2-yl)piperazin-1-yl)ethyl]pyrido[4',3':4,5]-thieno[2,3-d]pyrimidin-4-one, $^1$H NMR (270 MHz, CDCl$_3$): 0.6 (s, 4H), 1.9 (p, 1H), 2.4 (s, 3H), 2.6 (t, 4H), 2.7 (t, 2H), 4.1 (t, 2H), 6.4 (d, 1H), 6.5 (d, 1H), 7.4 (t, 1H), 8.0 (s, 1H)

179. 3,4,5,6,7,8-Hexahydro-7-methyl-3-[4-(4-(3-thiomethylphenyl)piperazin-1-yl)butyl]pyrido[4',3':4,5]thieno-[2,3-d]pyrimidin-4-one, ESI MS: [M+H]$^+$=456

180. 3,4,5,6,7,8-Hexahydro-7-(4-chlorobenzyl)-3-[2-(4-(3-trifluoromethylphenyl)piperazin-1-yl)ethyl]pyrido-[4',3':4,5]thieno[2,3-d]pyrimidin-4-one, EI MS: [M]$^+$=587

181. 3,4,5,6,7,8-Hexahydro-7-(4-methoxybenzyl)-3-[2-(4-(3-trifluoromethylphenyl)piperazin-1-yl)ethyl]pyrido-[4',3':4,5]thieno[2,3-d]pyrimidin-4-one×3 HCl, EI MS: [M]$^+$=583

182. 3,4,5,6,7,8-Hexahydro-7-benzyl-3-[2-(4-(3-trifluoromethylphenyl)piperazin-1-yl)ethyl]pyrido[4',3':4,5]-thieno-[2,3-d]pyrimidin-4-one×3 HCl, ESI MS: [M+H]$^+$=554

183. 3,4,5,6,7,8-Hexahydro-7-(2-phenylethyl)-3-[2-(4-(3-trifluoromethylphenyl)piperazin-1-yl)ethyl]pyrido-[4',3':4,5]thieno[2,3-d]pyrimidin-4-one, ESI MS: [M+H]$^+$=568

184. 3,4,5,6,7,8-Hexahydro-7-(2-(4-methoxyphenyl)ethyl)-3-[2-(4-(3-trifluoromethylphenyl)piperazin-1-yl)ethyl]-pyrido[4',3':4,5]thieno[2,3-d]pyrimidin-4-one, ESI MS: [M+H]$^+$=598

185. 3,4,5,6,7,8-Hexahydro-7-ethyl-3-[2-(4-(3-trifluoromethylphenyl)piperazin-1-yl)ethyl]pyrido[4',3':4,5]thieno-[2,3-d]pyrimidin-4-one, ESI MS: [M+H]$^+$=492

186. 3,4,5,6,7,8-Hexahydro-7-acetyl-3-[2-(4-(3-trifluoromethylphenyl)piperazin-1-yl)ethyl]pyrido[4',3':4,5]thieno-[2,3-d]pyrimidin-4-one, ESI MS: [M+H]$^+$=506

187. 3,4,5,6,7,8-Hexahydro-7-benzoyl-3-[2-(4-(3-trifluoromethylphenyl)piperazin-1-yl)ethyl]pyrido[4',3':4,5]thieno-[2,3-d]pyrimidin-4-one, ESI MS: [M+H]$^+$=568

188. 3,4,5,6,7,8-Hexahydro-7-(2-(4-chlorophenyl)ethyl)-3-[2-(4-(3-trifluoromethylphenyl)piperazin-1-yl)ethyl]pyrido[4',3':4,5]thieno[2,3-d]pyrimidin-4-one, ESI MS: [M]$^+$=602

189. 3,4,5,6,7,8-Hexahydro-7-(3-benzoylpropyl)-3-[2-(4-(3-trifluoromethylphenyl)piperazin-1-yl)ethyl]pyrido-[4',3':4,5]thieno[2,3-d]pyrimidin-4-one×3 HCl, ESI MS: [M+H]$^+$=610

190. 3,4,5,6,7,8-Hexahydro-7-(4-nitrobenzyl)-3-[2-(4-(3-trifluoromethylphenyl)piperazin-1-yl)ethyl]pyrido-[4',3':4,5]thieno[2,3-d]pyrimidin-4-one, ESI MS: [M+H]$^+$=599

191. 3,4,5,6,7,8-Hexahydro-7-(3-phenylpropyl)-3-[2-(4-(3-trifluoromethylphenyl)piperazin-1-yl)ethyl]pyrido-[4',3':4,5]thieno[2,3-d]pyrimidin-4-one×3 HCl, ESI MS: [M+H]$^+$=582

192. 3,4,5,6,7,8-Hexahydro-7-(2-benzamidoethyl)-3-[2-(4-(3-trifluoromethylphenyl)piperazin-1-yl)ethyl]pyrido-[4',3':4,5]thieno[2,3-d]pyrimidin-4-one, $^1$H NMR (270 MHz, CDCl$_3$): 2.8–3.0 (m, 10H), 3.2 (m, 6H), 4.1 (t, 2H), 6.8 (s, 1H), 7.1 (m, 3H), 7.3–7.6 (m, 4H), 7.8 (d, 2H), 8.0 (s, 1H)

193. 3,4,5,6,7,8-Hexahydro-7-methyl-3-[3-(4-(3-methylphenyl)-piperazin-1-yl)propyl]pyrido[4',3':4,5]-thieno[2,3-d]-pyrimidin-4-one, ESI MS: [M+H]$^+$=438

194. 3,4,5,6,7,8-Hexahydro-7-methyl-3-[3-(4-(3-chlorophenyl)-piperazin-1-yl)propyl]pyrido[4',3':4,5]-thieno[2,3-d]-pyrimidin-4-one, ESI MS: [M]$^+$=458

195. 3,4,5,6,7,8-Hexahydro-7-methyl-3-[2-(4-(3-methylphenyl)-piperazin-1-yl)ethyl]pyrido[4',3':4,5]-thieno[2,3-d]-pyrirmidin-4-one, ESI MS: [M+H]$^+$=424

196. 3,4,5,6,7,8-Hexahydro-7-methyl-3-[2-(4-(2-chloro-4-trifluoromethylpyridin-6-yl)piperazin-1-yl)ethyl]pyrido-[4',3':4,5]thieno[2,3-d]pyrimidin-4-one, $^1$H NMR (400 MHz, CDCl$_3$): 2.5 (s, 3H), 2.8 (m, 4H), 3.2 (m, 2H), 3.6 (m, 6H), 4.1 (t, 2H), 6.6 (s, 1H), 6.8 (s, 1H), 8.0 (s, 1H)

197. 3,4,5,6,7,8-Hexahydro-7-methyl-3-[2-(4-(3-chlorophenyl)-piperazin-1-yl)ethyl]pyrido[4',3':4,5]-thieno[2,3-d]-pyrimidin-4-one, $^1$H NMR (400 MHz, CDCl$_3$): 2.5 (s, 3H), 2.6 (t, 4H), 2.7–2.9 (m, 4H), 3.2 (m, 6H), 3.6 (s, 2H), 4.1 (t, 2H), 6.7–6.9 (m, 3H), 7.2 (t, 1H), 8.0 (s, 1H)

198. 3,4,5,6,7,8-Hexahydro-7-methyl-3-[4-(4-(4-chlorophenyl)-piperazin-1-yl)butyl]pyrido[4',3':4,5]-thieno[2,3-d]-pyrimidin-4-one, ESI MS: [M+H]$^+$=472

199. 3,4,5,6,7,8-Hexahydro-7-isopropyl-3-[2-(4-(3-trifluoromethyl-4-chlorophenyl)piperazin-1-yl)ethyl]pyrido-[4',3':4,5]thieno[2,3-d]pyrimidin-4-one×HCl, $^1$H NMR (400 MHz, CDCl$_3$): 1.1 (d, 6H), 3.1 (m, 6H), 3.8 (s, 2H), 4.1 (t, 2H), 6.9 (dd, 1H), 7.1 (d, 1H), 7.3 (d, 1H), 7.9 (s, 1H)

200. 3,4,5,6,7,8-Hexahydro-7-methyl-3-[4-(4-(3-trifluoromethylphenyl)piperazin-1-yl)butyl]pyrido[4',3':4,5]thieno-[2,3-d]pyrimidin-4-one, ESI MS: [M+H]$^+$=506

201. 3,4,5,6,7,8-Hexahydro-7-methyl-3-[3-(4-(3-trifluoromethylphenyl)piperazin-1-yl)propyl]pyrido[4',3':4,5]thieno-[2,3-d]pyrimidin-4-one, ESI MS: [M+H]$^+$=492

202. 3,4,5,6,7,8-Hexahydro-7-methyl-3-[3-(4-(isoquinolin-1-yl)-piperazin-1-yl)propyl]pyrido[4',3':4,5]thieno[2,3-d]-pyrimidin-4-one 203. 3,4,5,6,7,8-Hexahydro-7-methyl-3-[4-(4-(isoquinolin-1-yl)-piperazin-1-yl)butyl]pyrido[4',3':4,5]thieno[2,3-d]-pyrimidin-4-one 204. 3,4,5,6,7,8-Hexahydro-3-[2-(4-(isoquinolin-1-yl)-piperazin-1-yl)ethyl]pyrido[4',3':4,5]thieno[2,3-d]-pyrimidin-4-one 205. 3,4,5,6,7,8-Hexahydro-7-acetyl-3-[2-(4-(isoquinolin-1-yl)-piperazin-1-yl)ethyl]pyrido[4',3';4,5]thieno[2,3-d]-pyrimidin-4-one 206. 3,4,5,6,7,8-Hexahydro-7-ethyl-3-[2-(4-(isoquinolin-1-yl)-piperazin-1-yl)ethyl]pyrido[4',3':4,5]thieno[2,3-d]-pyrimidin-4-one 207. 3,4,5,6,7,8-Hexahydro-7-propyl-3-[2-(4-(isoquinolin-1-yl)-piperazin-1-yl)ethyl]pyrido[4',3':4,5]thieno[2,3-d]-pyrimidin-4-one
208. 3,4,5,6,7,8-Hexahydro-7-cyclopropyl-3-[2-(4-(isoquinolin-1-yl)piperazin-1-yl)ethyl]pyrido[4',3':4,5]thieno-[2,3-d]pyrimidin-4-one
209. 3,4,5,6,7,8-Hexahydro-7-cyclopropylmethyl-3-[2-(4-(isoquinolin-1-yl)piperazin-1-yl)ethyl]pyrido-[4',3':4,5]thieno[2,3-d]pyrimidin-4-one These compounds are suitable for treating central nervous system-related emotional disturbances such as seasonal affective disturbances and dysthymia. These disturbances also include anxiety states such as generalized anxiety, panic attacks, sociophobia, obsessional neuroses and post-traumatic stress symptoms, disturbances of the memory, including dementia, amnesias and age-related loss of memory, and also psychogenic eating disturbances such as anorexia nervosa and bulimia nervosa.

DE 1973444.5 describes 3-substituted 3,4,5,7-tetrahydropyrrolo[3',4':4,5]thieno[2,3-d]pyrimidine derivatives of the formula I

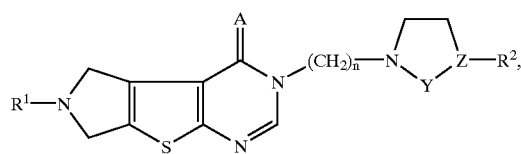

where
- $R^1$ is hydrogen, a $C_1$–$C_4$-alkyl group, an acetyl group, a phenylalkyl $C_1$–$C_4$ radical, with the aromatic moiety optionally being substituted by halogen, or $C_1$–$C_4$-alkyl, trifluoromethyl, hydroxyl, $C_1$–$C_4$-alkoxy, amino, cyano or nitro groups, or a carboxylic-$C_1$–$C_3$-alkyl ester radical,
- $R^2$ is a phenyl, pyridyl, pyrimidinyl or pyrazinyl group which is optionally monosubstituted or disubstituted by halogen atoms, $C_1$–$C_4$-alkyl, or trifluoromethyl, trifluoromethoxy, hydroxyl, $C_1$–$C_4$-alkoxy, amino, monomethylamino, dimethylamino, cyano or nitro groups, and which can optionally be fused to a benzene nucleus which can optionally be monosubstituted or disubstituted by halogen atoms, or $C_1$–$C_4$-alkyl, hydroxy, trifluoromethyl, $C_1$–$C_4$-alkoxy, amino, cyano or nitro groups, and which can optionally contain 1 nitrogen atom, or to a 5- or 6-membered ring which can contain 1–2 oxygen atoms,
- A is NH or oxygen,
- Y is $CH_2$, $CH_2$—$CH_2$, $CH_2$—$CH_2$—$CH_2$ or $CH_2$—$CH$,
- Z is nitrogen, carbon or CH, with it also being possible for the bond between Y and Z to be a double bond,
- and n is the number 2, 3 or 4.

These compounds of the formula I can be prepared by reacting a compound of the formula II

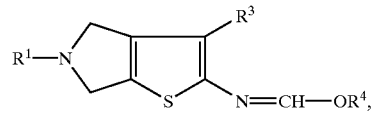

in which $R^1$ has the abovementioned meanings, $R^3$ is a cyano group or a $C_{1-3}$-alkyl-carboxylic ester group, and $R^4$ is $C_{1-3}$-alkyl, with a primary amine of the formula III

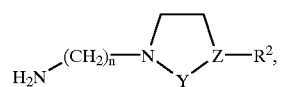

where $R^2$ has the abovementioned meanings, and optionally converting the resulting compound into the acid addition salt of a physiologically tolerated acid.

The reaction expediently takes place in an inert organic solvent, in particular a lower alcohol, e.g. methanol or ethanol, or a cyclic, saturated ether, in particular tetrahydrofuran or dioxane.

As a rule, the reaction takes place at from 20 to 110° C., in particular from 60 to 90° C., and has generally finished within from 1 to 10 hours.

Or, a compound of the formula II

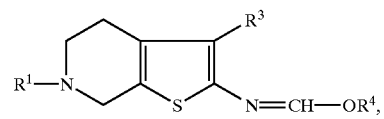

in which $R^1$ has the abovementioned meanings, $R^3$ is a cyano group or a $C_{1-3}$-alkyl-carboxylic ester group, and $R^4$ is $C_{1-3}$-alkyl, is reacted with a primary aminoalcohol of the formula IV

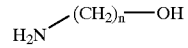

in an inert solvent, preferably alcohols such as ethanol, at from 60° to 120° C., to give the cyclization product V (X=OH)

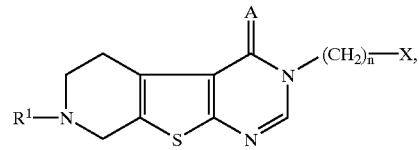

which is then converted into the corresponding halogen derivative V (X=Cl, Br) using a halogenating agent, such as thionyl chloride or hydrobromic acid, in an organic solvent, such as a halogenohydrocarbon, or without any solvent, at from room temperature to 100° C. Finally, the halogen derivative of the formula V (X=Cl, Br) is reacted with an amine of the formula VI

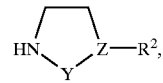

where Y, Z and $R^2$ have the abovementioned meanings, to give the novel end product of the formula I. This reaction proceeds most efficiently in an inert organic solvent, preferably toluene or xylene, in the presence of a base, such as potassium carbonate or potassium hydroxide, at from 60° C. to 150° C.

The novel compounds of the formula I can be purified either by recrystallization from the customary organic solvents, preferably from a lower alcohol, such as ethanol, or by means of column chromatography.

The free 3-substituted 3,4,5,7-tetrahydropyrrolo[3',4':4,5]-thieno[2,3-d]pyrimidine derivatives of the formula I can be converted in the customary manner into the acid addition salts of a solution using the stoichiometric quantity of the corresponding acid. Examples of pharmaceutically tolerated acids are hydrochloric acid, phosphoric acid, sulfuric acid, methanesulfonic acid, amidosulfonic acid, maleic acid, fumaric acid, oxalic acid, tartaric acid and citric acid.

The following Examples serve to clarify the invention:

A Preparation of the starting materials a) 2-Amino-3,5-dicarboethoxy-4,6-dihydrothieno[3,2-c] pyrrole 16.1 ml (150 mmol) of ethyl cyanoacetate and 4.8 g (150 mmol) of powdered sulfur were added to 23.6 g (150 mmol) of ethyl pyrrolidin-3-one-1-carboxylate (Kuhn, Osswald: Chem. Ber. 89, 1435 (1956)) in 60 ml of ethanol, after which 15.6 ml (112 mmol) of triethylamine were added dropwise under a nitrogen atmosphere and while stirring thoroughly. The mixture was then left to stir overnight at room temperature. After the mixture had been evaporated, the residue was dissolved in 70 ml of ethyl acetate and the solution was left to crystallize while stirring. After cooling, the crystals were filtered off with suction while being rewashed with a small quantity of cold ethyl acetate. 13.2 g (31%) of product having a m.p. of 154–156° C. were isolated.

b) 2-Ethoxymethyleneamino-3,5-dicarboethoxy-4,6-dihydrothieno-[3,2-c]pyrrole 0.3 ml of acetic anhydride was added to 1.4 g (4.8 mmol) of 2-amino-3,5-dicarboethoxy-4,6-dihydrothieno[3,2-c]pyrrole in 14 ml of triethyl orthoformate, and the mixture was boiled under nitrogen and at reflux for 1 h. After that, the mixture was evaporated right down at 80° C. on a rotary evaporator. 1.6 g (99%) of crude product were isolated as a viscous oil, which is sufficiently pure for further reaction.

c) 3-(2-Hydroxyethyl)-6-carboethoxy-3,4,5,7-tetrahydropyrrolo-[3',4':4,5]thieno[2,3-d]pyrimidin-4-one 13 ml (215 mmol) of ethanolamine were added to 15.5 g (46 mmol) of 2-ethoxymethyleneamino-3-carboethoxy-5-ethyl-4,5,6,7-tetrahydrothieno[3,2-c]pyridine in 250 ml of ethanol, and the mixture was boiled at reflux for 3 h. It was then left to cool down and was stirred thoroughly in an icebath. The fine solids which had precipitated out were filtered off with suction and rewashed with cold ethyl acetate. 5.5 g (36%) of a pale brown product were isolated. M.p. 243–245° C.

d) 3-(2-Chloroethyl)-6-carboethoxy-3,4,5,7-tetrahydropyrrolo-[3',4':4,5]thieno[2,3-d]pyrimidin-4-one 5.5 g (17.8 mmol) of 3-(2-hydroxyethyl)-6-ethyl-3,4,5,6,7,8-hexahydropyrido[3',4':4,5]thieno[2,3-d]pyrimidin-4-one in 50 ml of 1,2-dichloroethane were heated to reflux (slow dissolution), after which 2 ml (27 mmol) of thionyl chloride in 10 ml of 1,2-dichloroethane were added dropwise. After 1 h of reflux boiling, the reaction mixture was evaporated, after which the residue was stirred thoroughly in a little dichloromethane and the solids were filtered off with suction. 5.4 g (92%) of product were isolated, with this product being sufficiently pure for the subsequent reactions, m.p. 169–171° C.

e) N-(1-Naphthyl)piperazine 83.2 g (966 mmol) of piperazine, 38.0 g (339 mmol) of potassium tert-butoxide and 50.0 g (241 mmol) of 1-bromonaphthalene were added to a mixture of 5,4 g (24.2 mmol) of palladium acetate and 14.7 g (48.3 mmol) of tri-o-tolylphosphipe in 500 ml of xylene, and the reaction mixture was heated at reflux for 10 h, while stirring thoroughly and under a nitrogen atmosphere. After that, the mixture was diluted with methylene chloride, the insoluble residues were filtered off and the filtrate was evaporated. The crude product was purified by column chromatography (silica gel, eluent THF/methanol/ammonia 85/13/2). 21.5 g (42%) of product having a m.p. of 84–86° C. were isolated.

f) N-(2-Methyl-1-naphthyl)piperazine 14.7 g (82.7 mmol) of bis(2-chloroethyl)amine×HCl were added to 13.0 g (82.7 mmol) of 1-amino-2-methylnaphthalene in 100 ml of chlorobenzene, and the mixture was boiled under nitrogen and at reflux for 90 h. The mixture was then evaporated and the residue was partitioned between methylene chloride and water at pH=9; the organic phase was then evaporated after having been dried. The crude product was purified by column chromatography (silica gel, eluent THF/methanol/ammonia 85/13/2). 11.6 g (62%) of product were isolated.

g) 4-Piperazin-1-ylisoquinoline 4.51 g (21.7 mmol) of 4-bromoisoquinoline, 4.65 g (25.0 mmol) of t-butyl piperazine-N-carboxylate, 0.1 g (0.11 mmol) of tris(dibenzylideneacetone)dipalladium, 0.11 g (0.18 mmol) of 2,2'-bis(diphenylphosphino)-1,1'-binaphthyl and 2.92 g (30.4 mmol) of sodium tert-butoxide were together added to 50 ml of toluene, and the mixture was stirred at 75° C. for 2 h. The reaction mixture was added to ice/sodium chloride, and this latter mixture was then extracted with ethyl acetate, after which the organic phase was dried over sodium sulfate and the solvent was removed on a rotary evaporator. The product crystallized out and was then filtered off with suction and washed with pentane. 5.5 g (81%) of the Boc-protected piperazine were obtained (m.p.; 111° C.). 5.2 g (16.6 mmol) of this substance were taken up in 17 ml of dichloromethane, after which 17 ml (0.22 mmol) of trifluoroacetic acid were added slowly to this solution at 0° C. The mixture was left to stir at 0° C. for 4 h, after which it was poured onto ice water and this latter mixture was then extracted with dichloromethane. The aqueous phase was filtered, rendered alkaline and then extracted with dichloromethane. After having dried over sodium sulfate, and to a large extent removed the solvent, dilution took place with diethyl ether and the hydrochloride was precipitated with ethereal hydrochloric acid. This resulted in 3.2 g (67%) of the product, having a m.p. of 293–294° C.

Insofar as they were not known from the literature (cf. Patent Application DE 19636769.7 as well), additional piperazine derivatives (see Examples) were prepared in analogy with e), f) and g).

B Preparation of the end products

EXAMPLE 1

3,4,5,7-Tetrahydro-6-carboethoxy-3-[2-(4-(2-methoxyphenyl)-piperazin-1-yl)ethyl]pyrrolo[3',4':4,5]thieno[2,3-d]pyrimidin-4-one 1.1 g (4.8 mmol) of 1-(2-aminoethyl)-4-(2-methoxyphenyl)-piperazine were added to 1.6 g (4.8 mmol) of 2-ethoxymethylene-amino-3,5-dicarboethoxy-4,6-dihydrothieno-[3,2-c]pyrrole in 25 ml of ethanol, and the mixture was boiled at reflux for 2 h. After that, the mixture was evaporated on a rotary evaporator and the crude product was purified by column chromatography (silica gel, eluent methylene chloride/methanol 96/4). 1.1 g (47%) of product, having a m.p. of 153–155° C., were isolated after recrystallization from ethyl acetate.

EXAMPLE 2

0.7 g (3.0 mmol) of N-(1-naphthyl)homopiperazine and 0.5 g (3.6 mmol) of finely powdered potassium carbonate were added to 1.0 g (3.0 mmol) of 3-(2-chloroethyl)-6-carboethoxy-3,4,5,7-tetrahydropyrrolo[3',4':4,5]thieno[2,3d]pyrimidin-4-one in 40 ml of xylene, and the mixture was boiled under a nitrogen atmosphere and at reflux for a total of 70 h. The mixture was then evaporated in vacuo and the residue was partitioned at pH=10 between methylene chloride and water. After the organic phase had been dried and evaporated, the crude produce was purified by means of MPLC (eluent methanol/dichloromethane). 0.6 g (38% of hydrochloride, having a m.p. of 160° C. (decom.), was isolated by precipitation with ethereal hydrochloric acid from a solution of the product in acetone.

EXAMPLE 3

3,4,5,7-Tetrahydro-3-[2-(4-(1-naphthyl)piperazin-1-yl)ethyl]-pyrrolo[3',4':4,5]thieno[2,3-d]pyrimidin-4-one×2 HCl×2 H$_2$O 9.4 g (18.7 mmol) of 3,4,5,7-tetrahydro-6-carboethoxy-3-[2-(4-(1-naphthyl)piperazin-1-yl)ethyl]pyrrolo[3',4':4,5]-thieno[2,3-d]pyrimidin-4-one were introduced in a mixture of 80 ml of conc. hydrochloric acid and 80 ml of water and the whole was then boiled at reflux for 7 h. The reaction mixture was poured onto ice water and the resulting mixture was adjusted to pH=10 with conc. sodium hydroxide solution and extracted twice with methylene chloride. After having dried and evaporated the organic phase, the crude product was purified by column chromatography (silica gel, eluent methylene chloride/methanol 90/10). This resulted in the isolation of 2.4 g (30%) of product, which was dissolved in ethyl acetate and converted into the hydrochloride having a m.p. of 288–290° C. (decomp.).

EXAMPLE 4

3,4,5,7-Tetrahydro-6-ethyl-3-[2-(4-(1-naphthyl) piperazin-1-yl)-ethyl]pyrrolo[3',4':4,5]thieno[2,3-d] pyrimidin-4-one×2 HCl×3 H$_2$O 0.68 ml (8.5 mmol) of iodoethane and 0.5 g (3.5 mmol) of finely powdered potassium carbonate were added to 1.5 g (3.5 mmol) of 3,4,5,7-tetrahydro-3-[2-(4-(1-naphthyl) piperazin-1-yl)ethyl]- pyrrolo[3',4':4,5]thieno[2,3-d] pyrimidin-4-one in 30 ml of tetrahydrofuran, and the mixture was boiled at reflux for 3 h. The mixture was then poured onto ice/water and this resulting mixture was adjusted to pH=9 with ammonia and extracted twice with methylene chloride. After the organic phase had been dried and evaporated, the crude product was purified by column chromatography (silica gel, eluent methylene chloride/methanol 95/5). This resulted in the isolation of 0.4 g (25%) of product, which was dissolved in ethyl acetate and converted into the hydrochloride having a m.p. of 202–204° C. (decomp.).

EXAMPLE 5

3,4,5,7-Tetrahydro-6-acetyl-3-[2-(4-(1-naphthyl) piperazin-1-yl)-ethyl]pyrrolo[3',4':4,5]thieno[2,3-d] pyrimidin-4-one

EXAMPLE 6

3,4,5,7-Tetrahydro-6-benzyl-3-[2-(4-(1-naphthyl) piperazin-1-yl)-ethyl]pyrrolo[3',4':4,5]thieno[2,3-d] pyrimidin-4-one

EXAMPLE 7

3,4,5,7-Tetrahydro-6-(4-chlorophenyl-2-ethyl)-3-[2-(4-(1-naphthyl)piperazin-1-yl)ethyl]pyrrolo[3',4':4,5] thieno[2,3-d]-pyrimidin-4-one The following can be prepared in analogy with Examples 1 to 7:

8. 3,4,5,7-Tetrahydro-6-carboethoxy-3-[2-(4-(1-naphthyl)-piperazin-1-yl)ethyl]pyrrolo[3',4':4,5]thieno[2,3-d]-pyrimidin-4-one, m.p. 190–192° C.
9. 3,4,5,7-Tetrahydro-6-carboethoxy-3-[2-(4-(2-methyl-1-naphthyl)piperazin-1-yl)ethyl]pyrrolo[3',4':4,5]-thieno[2,3-d]pyrimidin-4-one
10. 3,4,5,7-Tetrahydro-6-carboethoxy-3-[2-(4-(2-methoxy-1-napthyl)piperazin-1-yl)ethyl]pyrrolo[3',4':4,5]-thieno[2,3-d]pyrimidin-4-one
11. 3,4,5,7-Tetrahydro-6-carboethoxy-3-[2-(4-pyrimidin-2-yl-piperazin-1-yl)ethyl]pyrrolo[3',4':4,5]thieno[2,3-d]-pyrimidin-4-one, m.p. 166° C.
12. 3,4,5,7-Tetrahydro-6-carboethoxy-3-[2-(4-(2-methoxyphenyl)-piperidin-1-yl)ethyl]pyrrolo[3',4':4,5] thieno[2,3-d]-pyrimidin-4-one
13. 3,4,5,7-Tetrahydro-3-[2-(4-(2-methoxyphenyl)-piperazin-1-yl)ethyl]pyrrolo[3',4':4,5]thieno[2,3-d]-pyrimidin-4-one
14. 3,4,5,7-Tetrahydro-3-[2-(4-naphth-1-ylhexahydro-1,4-diazepin-1-yl)ethyl]pyrrolo[3',4':4,5]thieno[2,3-d]-pyrimidin-4-one
15. 3,4,5,7-Tetrahydro-3-[2-(4-(2-methylphenyl)-piperazin-1-yl)-ethyl]pyrrolo[3',4':4,5]thieno[2,3-d]pyrimidin-4-one
16. 3,4,5,7-Tetrahydro-3-[2-(4-tetralin-5-yl-piperazin-1-yl) ethyl]pyrrolo[3',4':4,5]-thieno[2,3-d]pyrimidin-4-one
17. 3,4,5,7-Tetrahydro-3-[2-(4-indan-1-ylpiperazin-1-yl) ethyl]-pyrrolo[3',4':4,5]thieno[2,3-d]pyrimidin-4-one
18. 3,4,5,7-Tetrahydro-3-[2-(4-(2-methoxyphenyl)-3,4-dehydropiperidin-1-yl)ethyl]pyrrolo[3',4':4,5]-thieno[2,3-d]pyrimidin-4-one
19. 3,4,5,7-Tetrahydro-3-[2-(4-naphth-1-ylpiperidin-1-yl) ethyl]-pyrrolo[3',4':4,5]thieno[2,3-d]pyrimidin-4-one
20. 3,4,5,7-Tetrahydro-3-[2-(4-(2-methoxynaphth-1-yl-3,4-dehydropiperidin-1-yl)ethyl]pyrrolo[3',4':4,5]-thieno[2,3-d]pyrimidin-4-one
21. 3,4,5,7-Tetrahydro-6-ethyl-3-[2-(4-(2-methoxyphenyl)-piperazin-1-yl)ethyl]pyrrolo[3',4':4,5]thieno-[2,3-d] pyrimidin-4-one
22. 3,4,5,7-Tetrahydro-6-ethyl-3-[2-(4-(2,3-dimethylphenyl)-piperazin-1-yl)ethyl]pyrrolo[3',4':4,5] thieno-[2,3-d]pyrimidin-4-one
23. 3,4,5,7-Tetrahydro-6-ethyl-3-[2-(4-(2-chlorophenyl)-piperazin-1-yl)ethyl]pyrrolo[3',4':4,5]thieno-[2,3-d] pyrimidin-4-one
24. 3,4,5,7-Tetrahydro-6-ethyl-3-[2-(4-pyrimidin-2-yl-piperazin-1-yl)ethyl]pyrrolo[3',4':4,5]thieno[2,3-d]-pyrimidin-4-one
25. 3,4,5,7-Tetrahydro-6-ethyl-3-[2-(4-pyridin-2-yl-piperazin-1-yl)ethyl]pyrrolo[3',4':4,5]thieno[2,3-d]-pyrimidin-4-one 26. 3,4,5,7-Tetrahydro-6-ethyl-3-[2-(4-quinolin-2-yl-piperazin-1-yl)ethyl]pyrrolo[3',4':4,5]thieno[2,3-d]-pyrimidin-4-one
27. 3,4,5,7-Tetrahydro-6-ethyl-3-[2-(4-(2-methoxyphenyl)-piperidin-1-yl)ethyl]pyrrolo[3',4':4,5]thieno-[2,3-d] pyrimidin-4-one
28. 3,4,5,7-Tetrahydro-6-ethyl-3-[3-(4-pyrimidin-2-yl-piperazin-1-yl)propyl]pyrrolo[3',4':4,5]thieno[2,3-d]-pyrimidin-4-one
29. 3,4,5,7-Tetrahydro-6-methyl-3-[2-(4-(3-trifluoromethylphenyl)piperazin-1-yl)ethyl]pyrrolo[3',4':4,5]thieno-[2,3-d]pyrimidin-4-one
30. 3,4,5,7-Tetrahydro-6-methyl-3-[2-(4-(2-cyanophenyl)-piperazin-1-yl)ethyl]pyrrolo[3',4':4,5]thieno-[2,3-d] pyrimidin-4-one
31. 3,4,5,7-Tetrahydro-6-methyl-3-[2-(4-isoquinolin-4-yl-piperazin-1-yl)ethyl]pyrrolo[3',4':4,5]thieno-[2,3-d] pyrimidin-4-one
32. 3,4,5,7-Tetrahydro-6-methyl-3-[2-(4-naphth-1-yl-3,4-dehydropiperidin-1-yl)ethyl]pyrrolo[3',4':4,5]thieno-[2,3-d]pyrimidin-4-one
33. 3,4,5,7-Tetrahydro-6-acetyl-3-[2-(4-(2-methoxyphenyl)-piperazin-1-yl)ethyl]pyrrolo[3',4':4,5]thieno[2,3-d]-pyrimidin-4-one
34. 3,4,5,7-Tetrahydro-6-acetyl-3-[2-(4-(2-methyl-1-naphthyl)-piperazin-1-yl)ethyl]pyrrolo[3',4':4,5]thieno-[2,3-d]pyrimidin-4-one
35. 3,4,5,7-Tetrahydro-6-benzyl-3-[2-(4-(2-methoxyphenyl)-piperazin-1-yl)ethyl]pyrrolo[3',4':4,5]thieno-[2,3-d]pyrimidin-4-one
36. 3,4,5,7-Tetrahydro-6-(4-nitrophenyl-2-ethyl)-3-[2-(4-(1-naphthyl)piperazin-1-yl)ethyl]pyrrolo[3',4':4,5]thieno-[2,3-d]pyrimidin-4-one
37. 3,4,5,7-Tetrahydro-6-(4-aminobenzyl)-3-[2-(4-(2-methyl-1-naphthyl)piperazin-1-yl)ethyl]pyrrolo[3',4':4,5]thieno-[2,3-d]pyrimidin-4-one
38. 3,4,5,7-Tetrahydro-6-carboethoxy-3-[2-(4-(2-methylphenyl)-piperazin-1-yl)ethyl]pyrrolo[3',4':4,5]thieno-[2,3-d]pyrimidin-4-one, m.p. 152° C.
39. 3,4,5,7-Tetrahydro-6-carboethoxy-3-[2-(4-(2-chlorophenyl)-piperazin-1-yl)propyl]pyrrolo[3',4':4,5]thieno-[2,3-d]pyrimidin-4-one, m.p. 172° C.
40. 3,4,5,7-Tetrahydro-6-carboethoxy-3-[2-(4-(2-phenylpiperidin-1-yl)ethyl]pyrrolo[3',4':4,5]thieno[2,3-d]-pyrimidin-4-one
41. 3,4,5,7-Tetrahydro-6-carboethoxy-3-[2-(4-(2-naphth-1-yl-piperidin-1-yl)ethyl]pyrrolo[3',4':4,5]thieno[2,3-d]-pyrimidin-4-one
42. 3,4,5,7-Tetrahydro-6-carboethoxy-3-[2-(4-(2-naphth-1-yl-3,4-dehydropiperidin-1-yl)ethyl]pyrrolo[3',4':4,5]thieno[2,3-d]-pyrimidin-4-one
43. 3,4,5,7-Tetrahydro-6-carboethoxy-3-[3-(4-(2-cyanophenyl)-piperazin-1-yl)propyl]pyrrolo[3',4':4,5]thieno[2,3-d]-pyrimidin-4-one, m.p. 190° C.
44. 3,4,5,7-Tetrahydro-6-carboethoxy-3-[2-(4-indan-4-ylpiperazin-1-yl)ethyl]pyrrolo[3',4':4,5]thieno[2,3-d] pyrimidin-4-one, m.p. 149° C.

C Measuring receptor binding

Preparing the receptor-bearing cell membranes

The receptor binding studies were carried out using "membrane preparations" which were obtained from cell cultures of the human embryonic kidney cell line 293 (HEK 293) into which a specific serotonin receptor subtype (h5HT1A, h5HT1B or h5HT1D) has in each case been cloned and in which this subtype is permanently expressed.

The cells were grown in RPMI 1640 medium (Life Technologies), which additionally contained 10% fetal calf serum (FCS), 2 mmol of L-glutamine/l and 400 mg of geneticin G 418/l. The cells were incubated in so-called "tank stacks", at 37° C. in an incubator gassed with air/5% $CO_2$, until they had reached a confluent monolayer. The cells were then detached from the culture vessels using a buffer of the following composition: (values per liter) trypsin, 10 mg; EDTA, 4 mg; EGTA, 200 mg; KCl, 200 mg; $KH_2PO_4$, 200 mg; $Na_2HPO_4$, 1.15 g; NaCl, 8.0 g; pH 7.4. The cell suspension was pelleted and then resuspended in Dulbecco's phosphate-buffered saline (PBS); the cell density was then adjusted to approx. $10^8$ cells/ml. After the cells had been pelleted once again, the PBS was replaced by the same volume of ice-cold lysis buffer (5 mmol of tris/l; 10% glyzerol; pH 7.4) and the cells were incubated at 4° C. for 30 min. The lyzed cells (="membranes") were aliquoted and stored in liquid nitrogen until used in receptor binding studies. An aliquot was used per preparation for determining the protein content.

The novel compounds display a high affinity (K; $\leq$30 nM) for human $5\text{-}HT_{1A}$, $5\text{-}HT_{1B}$ and $5\text{-}HT_{1D}$ receptor types, which are expressed in cloned cell lines.

Receptor binding assay

The receptor binding studies were carried out in 1 ml Macrowell tubes which contained the following components:

50 µl of the test substance at differing concentrations for competition measurements or 50 µl of assay buffer or 50 µl of unlabeled serotonin (1 µmol/l final volume) for determining the total or non-specific binding control 200 µl of suspension of membranes of the appropriate receptor subtype having a protein content of 200 µg/tube 250 µl of radioligand solution ([$^3$H]5-carboxamidotryptamine (5-CT) for the h5HT1B and h5RT1D receptors or [$^3$H]8-hydroxydipropylaminotetralin (8-OH-DPAT) for the h5HT1A receptors. The final concentrations of the radioligands were adjusted to 3 nmol/l or 0.3 nmol/l.

The assay buffer (pH 7.4) had the following composition (per liter): tris, 6.057 g; $CaCl_2 \times 2H_2O$=5.88 g; ascorbic acid, 1 g; pargyline, 1.96 mg.

The assay mixture was incubated at 25° C. for 30 min and then filtered through a fiberglass filter (Whatman GF/B) using a cell harvesting appliance (Skatron), with the filters then being washed with from 5 to 9 ml of cold buffer. The filters were in each case placed, together with 5 ml of Ultima GoldxR liquid scintillator (Packard), in scintillation vials, which were shaken for 1 hour. The radioactivity was then determined in a beta counter (Wallac). The measurement data were evaluated by an iterative non-linear regression analysis using the "Statistical Analysis System (SAS)" which is similar-to the "LIGAND" program described by Munson and Rodbard (Anal. Biochem: 107, 220 (1980)). The competition constants ($K_i$) were recorded in nmol/l.

These compounds are suitable for treating central nervous system-related emotional disturbances such as seasonal affective disturbances and dysthymia. These disturbances also include anxiety states such as generalized anxiety, panic attacks, sociophobia, obsessional neuroses and post-traumatic stress symptoms, disturbances of the memory, including dementia, amnesias and age-related loss of memory, and also psychogenic eating disturbances such as anorexia nervosa and bulimia nervosa.

DE 19724980.9 describes 3-substituted 3,4-dihydrothieno-[2,3-d]pyrimidine derivatives of the formula I

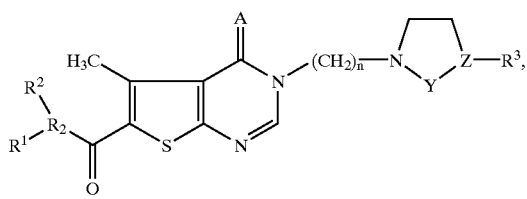

where

R$^1$ and R$^2$ are hydrogen or a C$_1$–C$_4$-alkyl group,

R$^3$ is a phenyl, pyridyl, pyrimidinyl or pyrazinyl group which is optionally monosubstituted or disubstituted by halogen atoms, C$_1$–C$_4$-alkyl, or trifluoromethylt trifluoromethoxy, hydroxy, C$_1$–C$_4$-alkoxy, amino, monomethylamino, dimethylamino, cyano or nitro groups, and which can optionally be fused to a benzene nucleus which can optionally be monosubstituted or disubstituted by halogen atoms, or C$_1$–C$_4$-alkyl, hydroxy, trifluoromethyl, C$_1$–C$_4$-alkoxy, amino, cyano or nitro groups and which can optionally contain 1 nitrogen atom, or to a 5- or 6-membered ring which can contain 1–2 oxygen atoms, A is NH or oxygen, Y is CH$_2$, CH$_2$—CH$_2$, CH$_2$—CH$_2$—CH$_2$ or CH$_2$—CH, Z is nitrogen, carbon or CH, with it also being possible for the bond between Y and Z to be a double bond, and n is the number 2, 3 or 4.

These compounds of the formula I can be prepared by reacting a compound of the formula II

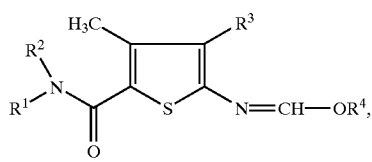

in which R$^1$ has the abovementioned meanings, R$^3$ is a cyano group or a C$_1$–$_3$-alkyl-carboxylic ester group, and R$^4$ is C$_1$–$_3$-alkyl, with a primary amine of the formula III

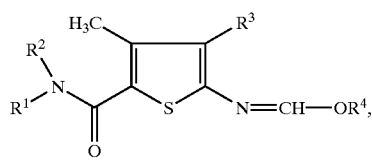

where R$^3$ has the abovementioned meanings, and optionally converting the resulting compound into the acid addition salt of a physiologically tolerated acid.

The reaction expediently takes place in an inert organic solvent, in particular a lower alcohol, e.g. methanol or ethanol, or a cyclic, saturated ether, in particular tetrahydrofuran or dioxane.

As a rule, the reaction takes place at from 20 to 110° C., in particular at from 60 to 90° C., and has generally finished within from 1 to 10 hours.

Or, a compound of the formula II

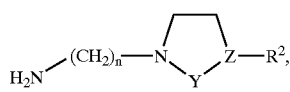

where R$^1$ has the abovementioned meaning, R$^3$ is a cyano group or a C$_1$–$_3$-alkyl-carboxylic ester group, and R$^4$ is C$_1$–$_3$-alkyl, is reacted with a primary aminoalcohol of the formula IV

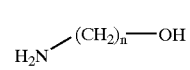

an inert solvent, preferably alcohols such as ethanol, at from 60° to 120° C., in order to give the cyclization product V (X=OH)

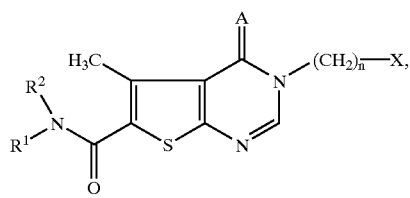

which is subsequently converted into the corresponding halogen derivative V (X=Cl, Br) using a halogenating agent such as thionyl chloride or hydrobromic acid, in an organic solvent such as a halogenohydrocarbon, or without any solvent, at from room temperature to 100° C. Finally, the halogen derivative of the formula V (X=Cl, Br) is reacted with an amine of the formula VI

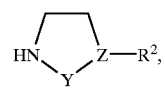

where Y, Z and R$^2$ have the abovementioned meanings, to give the novel end product of the formula I. This reaction proceeds most efficiently in an inert organic solvent, preferably toluene or xylene, in the presence of a base, such as potassium carbonate or potassium hydroxide, at from 60° C. to 150° C.

The novel compounds of the formula I can be purified either by recrystallization from the customary organic solvents, preferably from a lower alcohol, such as ethanol, or by means of column chromatography.

The free 3-substituted pyrido[3',4':4,5]thieno[2,3-d]-pyrimidine derivatives of the formula I can be converted, in the customary manner, into the acid addition salts of a solution using the stoichiometric quantity of the corresponding acid. Examples of pharmaceutically tolerated acids are hydrochloric acid, phosphoric acid, sulfuric acid, methanesulfonic acid, amidosulfuric acid, maleic acid, fumaric acid, oxalic acid, tartaric acid and citric acid.

The following Examples serve to clarify the invention:

A Preparation of the starting materials a) 2-Amino-3-carboethoxy-5-methyl-5-dimethylcarbamoyl-thiophene 82.8 ml (775 mmol) of ethyl cyanoacetate and 24.8 g (755 mmol) of powdered sulfur were added to 100 g (775 mmol) of dimethylacetoacetamide in 400 ml of ethanol, and, after that, 90 ml (647 mmol) of triethylamine were added dropwise under a nitrogen atmosphere and while stirring thoroughly. After 1 h, the mixture was heated to reflux for 8 h and was then subsequently left to stir overnight at room temperature. The mixture was evaporated under reduced pressure and the residue was taken up in 2 l of water; this solution was adjusted to pH=9 and extracted twice with methylene chloride. After the organic phase had been dried and evaporated, the crude product (70 g) was purified by dissolving it in 200 ml of boiling ethyl acetate. The solids which had precipitated out overnight in association with stirring were filtered off with suction, after cooling in an icebath, and rewashed several times with cold ethyl acetate. 39.0 g (20%) of product were isolated as gray solids having a m.p. of 122–124° C.

b) 2-Ethoxymethyleneamino-3-carboethoxy-4-methyl-5-dimethylcarbamoylthiophene 2.0 ml of acetic anhydride were added to 30.6 g (119 mmol) of 2-amino-3-carboethoxy-4-methyl-5-dimethylcarbamoyl-thiophene in 150 ml of triethyl orthoformate, and the mixture was boiled under nitrogen and at reflux for 2 h. The mixture was then evaporated right down at 80° C. on a rotary evaporator. 35.6 g (96%) of crude product were isolated as a dark oil, which is sufficiently pure for further reaction.

c) 3-(2-Hydroxyethyl)-5-methyl-6-dimethylcarbamoylthieno[2,3-d]-pyrimidin-4-one 8.0 ml (133 mmol) of ethanolamine were added to 35.6 g (114 mmol) of 2-ethoxymethyleneamino-3-carboethoxy-5-methyl-5-dimethylcarbamoylthiophene in 200 ml of ethanol, and the mixture was boiled at reflux for 2 h. The mixture was then evaporated under reduced pressure. 29.9 g (93%) of a dark viscous oil were isolated.

d) 3-(2-Chloroethyl)-5-methyl-6-dimethylcarbamoylthieno[2,3-d]-pyrimidin-4-one 29.9 g (106 mmol) of 3-(2-hydroxyethyl)-5-methyl-6-dimethylcarbamoylthieno[2,3-d]pyrimidin-4-one in 200 ml of 1,2-dichloroethane were heated to reflux (slow dissolution), after which 12.7 ml (175 mmol) of thionyl chloride in 20 ml of 1,2-dichloroethane were added dropwise. After 1 h of reflux boiling, the reaction mixture was evaporated after it had been cooled down. The crude product was partitioned between methylene chloride and water at pH=9. After the organic phase had been dried and evaporated, 44.1 g (83%) of product were isolated as a dark oil, which was purified by column chromatography (silica gel, eluent ethyl acetate). 23.8 g (76%) of product, having a m.p. of 120–122° C., were isolated.

Other $C_1$–$C_4$-mono- or dialkyl-carbamoyl derivatives of the formulae II and V can be prepared in analogy with the directions given in a) to d).

e) N-(1-Naphthyl)piperazine 83.2 g (966 mmol) of piperazine, 38.0 g (339 mmol) of potassium tert-butoxide and 50.0 g (241 mmol) of 1-bromonaphthalene were added to a mixture of 5.4 g (24.2 mmol) of palladium acetate and 14.7 g (48.3 mmol) of tri-o-tolylphosphine in 500 ml of xylene, and the reaction mixture was heated at reflux for 10 h under a nitrogen atmosphere and while stirring thoroughly. After that, the mixture was diluted with methylene chloride, the insoluble residues were filtered off and the filtrate was evaporated. The crude product was purified by column chromatography (silica gel, eluent THF/methanol/ammonia 85/13/2). 21.5 g (42%) of product having a m.p. of 84–86° C., were isolated.

f) N-(2-Methyl-1-naphthyl)piperazine 14.7 g (82.7 mmol) of bis(2-chloroethyl)amine×HCl were added to 13.0 g (82.7 mmol) of 1-amino-2-methylnaphthalene in 100 ml of chlorobenzene, and the mixture was boiled under nitrogen and at reflux for 90 h. The mixture was then evaporated and the residue was partitioned between methylene chloride and water at pH=9; the organic phase was then evaporated after having been dried. The crude product was purified by column chromatography (silica gel, eluent THF/methanol/ammonia 85/13/2). 11.6 g (62%) of product were isolated.

g) 4-Piperazin-1-ylisoquinoline 4.51 g (21.7 mmol) of 4-bromoisoquinoline, 4.65 g (25.0 mmol) of tert-butyl piperazine-N-carboxylate, 0.1 g (0.11 mmol) of tris(dibenzylideneacetone)dipalladium, 0.11 g (0.18 mmol) of 2,2'-bis(diphenylphosphino)-1,1'-binaphthyl and 2.92 g (30.4 mmol) of sodium tert-butoxide were together added to 50 ml of toluene and the mixture was stirred at 75° C. for 2 h. The reaction mixture was then added to ice/sodium chloride and this latter mixture was then extracted with ethyl acetate; the organic phase was then dried over sodium sulfate and the solvent was removed on a rotary evaporator. The product crystallized out and was filtered off with suction and washed with pentane. 5.5 g (81%) of the Boc-protected piperazine were obtained (m.p.: 111° C.). 5.2 g (16.6 mmol) of this substance were taken up in 17 ml of dichloromethane, and 17 ml (0.22 mmol) of trifluoroacetic acid were added slowly at 0° C. The mixture was left to stir at 0° C. for 4 h, after which it was poured onto ice water and the resulting mixture was extracted with dichloromethane. The aqueous phase was filtered, rendered alkaline and extracted with dichloromethane. After having dried over sodium sulfate and to a large extent having removed the solvent, dilution was effected with diethyl ether and the hydrochloride was precipitated with ethereal hydrochloric acid. This resulted in 3.2 g (67%) of the product having a m.p. of 293–294° C.

Insofar as they were not known from the literature (cf. Patent Application DE 19636769.7 as well), additional piperazine derivatives (see Examples) were prepared in analogy with e), f) and g).

B Preparation of the end products

EXAMPLE 1

3,4-Dihydro-5-methyl-6-dimethylcarbamoyl-3-[2-(4-(2-methoxyphenyl)piperazin-1-yl)ethyl]thieno[2,3-d]pyrimidin-4-one 1.9 g (8.0 mmol) of 1-(2-aminoethyl)-4-(2-methoxyphenyl)piperazine were added to 2.4 g (7.8 mmol) of 2-ethoxymethyleneamino-3-carboethoxy-4-methyl-5-dimethylcarbamoylthiophene in 30 ml of ethanol, and the mixture was boiled at reflux for 2 h. After standing overnight, the product crystallized out and was filtered off with suction and washed with a little ethanol. 2.2 g (62%) of product, having a m.p. of 188–190° C., were isolated.

EXAMPLE 2

3,4-Dihydro-5-methyl-6-dimethylcarbamoyl-3-[2-(4-(2,3-dimethyl-phenyl)piperazin-1-yl)ethyl]thieno[2,3-d]pyrimidin-4-one 1.1 g (5.0 mmol) of 1-(2,3-dimethylphenyl)piperazine hydrochloride and 1.54 ml (11 mmol) of triethylamine were added to 1.5 g (5.0 mmol) of 3-(2-chloroethyl)-5-methyl-6-dimethylcarbamoylthieno[2,3-d]pyrimidin-4-one in 15 ml of dimethylformamide, and the mixture was heated, at 125° C. and under nitrogen, for a total of 3 h. After the mixture had been poured into water, the resulting mixture was extracted with ethyl acetate, after which the organic phase was extracted at pH=2 with dilute hydrochloric acid; the aqueous phase which resulted from this was rendered basic with dilute sodium hydroxide solution. The crude product was extracted with dichloromethane, after which drying took place over sodium sulfate and the solvent was removed under reduced pressure. The oily residue was crystallized from a little methanol and filtered off with suction. This resulted in 0.7 g (31%) of product having a m.p. of 160–161° C.

The following were prepared in analogy with Examples 1 and 2:

3. 3,4-Dihydro-5-methyl-6-dimethylcarbamoyl-3-[2-(4-(1-naphthyl)piperazin-1-yl)ethyl]thieno[2,3-d]pyrimidin-4-one, m.p. 190–191° C.
4. 3,4-Dihydro-5-methyl-6-dimethylcarbamoyl-3-[2-(4-(2-methyl-1-naphthyl)piperazin-1-yl)ethyl]-thieno[2,3-d]pyrimidin-4-one, m.p. 178–180° C.
5. 3,4-Dihydro-5-methyl-6-dimethylcarbamoyl-3-[2-(4-(2-methoxy-1-naphthyl)piperazin-1-yl)ethyl]-thieno[2,3-d]pyrimidin-4-one×H$_2$O, m.p. 153–155° C. (decomp.)
6. 3,4-Dihydro-5-methyl-6-dimethylcarbamoyl-3-[2-(4-(2-methylphenyl)piperazin-1-yl)ethyl]-thieno[2,3-d]pyrimidin-4-one
7. 3,4-Dihydro-5-methyl-6-dimethylcarbamoyl-3-[2-(4-(3-trifluoromethylphenyl)piperazin-1-yl)ethyl]thieno[2,3-d]-pyrimidin-4-one, m.p. 146° C.
8. 3,4-Dihydro-5-methyl-6-dimethylcarbamoyl-3-[2-(4-(2-chlorophenyl)piperazin-1-yl)ethyl]thieno[2,3-d]pyrimidin-4-one
9. 3,4-Dihydro-5-methyl-6-dimethylcarbamoyl-3-[2-(4-pyrimidin-2-ylpiperazin-1-yl)ethyl]thieno-[2,3-d]pyrimidin-4-one×2HCl×4 H$_2$O, m.p. 180–182° C. (decomp.)
10. 3,4-Dihydro-5-methyl-6-dimethylcarbamoyl-3-[2-(4-pyridin-2-ylpiperazin-1-yl ) ethyl] thieno[ 2, 3-d]pyriidin-4-one
11. 3,4-Dihydro-5-methyl-6-dimethylcarbamoyl-3-[2-(4-quinolin-2-ylpiperazin-1-yl)ethyl]thieno[2,3-d]pyrimidin-4-one
12. 3,4-Dihydro-5-methyl-6-dimethylcarbamoyl-3-[2-(4-(3,5-dichlorophenyl)piperazin-1-yl)ethyl]thieno[2,3-d]-pyrimidin-4-one
13. 3,4-Dihydro-5-methyl-6-dimethylcarbamoyl-3-[2-(4-tetralin-5-ylpiperazin-1-yl)ethyl]thieno[2,3-d]pyrimidin-4-one, m.p. 174° C.
14. 3,4-Dihydro-5-methyl-6-dimethylcarbamoyl-3-[2-(4-indan-4-ylpiperazin-1-yl)ethyl]thieno[2,3-d]pyrimidin-4-one, m.p. 153° C.
15. 3,4-Dihydro-5-methyl-6-dimethylcarbamoyl-3-[2-(4-(2-cyanophenyl)piperazin-1-yl)ethyl]thieno[2,3-d]pyrimidin-4-one, m.p. 210° C. (hydrochloride)
16. 3,4-Dihydro-5-methyl-6-dimethylcarbamoyl-3-[2-(4-isoquinolin-4-ylpiperazin-1-yl)ethyl]thieno[2,3-d]pyrimidin-4-one
17. 3,4-Dihydro-5-methyl-6-dimethylcarbamoyl-3-[3-(4-pyrimidin-2-ylpiperazin-1-yl)propyl]thieno[2,3-d]pyrimidin-4-one×2 HCl×2 H$_2$O, m.p. 209–211° C. (decomp.)
18. 3,4-Dihydro-5-methyl-6-dimethylcarbamoyl-3-[2-(4-(2-methoxyphenyl)piperidin-1-yl)ethyl]thieno[2,3-d]pyrimidin-4-one
19. 3,4-Dihydro-5-methyl-6-dimethylcarbamoyl-3-[2-(4-(2-methoxyphenyl)-3,4-dihydropiperidin-1-yl)ethyl]thieno-[2,3-d]pyrimidin-4-one
20. 3,4-Dihydro-5-methyl-6-dimethylcarbamoyl-3-[3-(4-(3-trifluoromethylphenyl)piperazin-1-yl)propyl]thieno-[2,3-d]pyrimidin-4-one×2 HCl, m.p. 122–125° C.
21. 3,4-Dihydro-5-methyl-6-dimethylcarbamoyl-3-[2-(4-naphth-1-ylpiperidin-1-yl)ethyl]thieno[2,3-d]pyrimidin-4-one
22. 3,4-Dihydro-5-methyl-6-dimethylcarbamoyl-3-[2-(4-(2-methoxynaphth-1-yl)-3,4-dehydropiperidin-1-yl)ethyl]-thieno[2,3-d]pyrimidin-4-one
23. 3,4-Dihydro-5-methyl-6-dimethylcarbamoyl-3-[2-(4-naphth-1-yl-1,4-hexahydro-1,4-diazepin-1-yl)ethyl]-thieno[2,3-d]pyrimidin-4-one, m.p. 225–230° C. (hydrochloride)
24. 3,4-Dihydro-5-methyl-6-carbamoyl-3-[2-(4-(1-naphthyl)-piperazin-1-yl)ethyl]thieno[2,3-d]pyrimidin-4-one
25. 3,4-Dihydro-5-methyl-6-carbamoyl-3-[2-(4-pyrimidin-2-yl-piperazin-1-yl)ethyl]thieno[2,3-d]pyrimidin-4-one
26. 3,4-Dihydro-5-methyl-6-diethylcarbamoyl-3-[2-(4-(2-methoxyphenyl)piperazin-1-yl)ethyl]thieno[2,3-d]pyrimidin-4-one
27. 3,4-Dihydro-5-methyl-6-diethylcarbamoyl-3-[2-(4-(1-naphthyl)-piperazin-1-yl)ethyl]thieno[2,3-d]pyrimidin-4-one
28. 3,4-Dihydro-5-methyl-6-diethylcarbamoyl-3-[2-(4-pyrimidin-2-ylpiperazin-1-yl)ethyl]thieno[2,3-d]pyrimidin-4-one
29. 3,4-Dihydro-5-methyl-6-dimethylcarbamoyl-3-[2-(4-quinazolin-4-ylpiperazin-1-yl)ethyl]thieno[2,3-d]pyrimidin-4-one, m.p. 295 - 300° C. (hydrochloride)
30. 3,4-Dihydro-5-methyl-6-dimethylcarbamoyl-3-[2-(4-(2,4-dimethoxyphenyl)piperazin-1-yl)ethyl]thieno-[2,3-d]pyrimidin-4-one, m.p. 170–171° C.
31. 3,4-Dihydro-5-methyl-6-dimethylcarbamoyl-3-[2-(4-(2,5-dimethylphenyl)piperazin-1-yl)ethyl]thieno-[2,3-d]pyrimidin-4-one, m.p. 90–91° C.
32. 3,4-Dihydro-5-methyl-6-dimethylcarbamoyl-3-[2-(4-naphth-1-yl-3,4-dehydropiperidin-1-yl)ethyl]thieno[2,3-d]pyrimidin-4-one, MS: m$^+$=509.1

These compounds are suitable for treating central nervous system-related emotional disturbances such as seasonal affective disturbances and dysthymia. These disturbances also include anxiety states such as generalized anxiety, panic attacks, sociophobia, obsessional neuroses and post-traumatic stress symptoms, disturbances of the memory, including dementia, amnesias and age-related loss of memory, and also psychogenic eating disturbances such as anorexia nervosa and bulimia nervosa.

DE 19724979.5 describes 3-substituted 3,4,5,6,7,8-hexahydropyrido[3',4':4,5]thieno[2,3-d]pyrimidine derivatties of the formula I

I

[Structure of formula I: R¹–N in piperidine ring fused to thieno[2,3-d]pyrimidinone with A substituent, (CH₂)ₙ–N linked to Y–Z–R²]

where
- R¹ is hydrogen, a $C_1$–$C_4$-alkyl group, an acetyl group, a phenylalkyl $C_1$–$C_4$ radical, with the aromatic moiety optionally being substituted by halogen or $C_1$–$C_4$-alkyl, trifluoromethyl, hydroxyl, $C_1$–$C_4$-alkoxy, amino, cyano or nitro groups, or a phenylalkanone radical, with it being possible for the phenyl group to be substituted by halogen,
- R² is a phenyl, pyridyl, pyrimidinyl or pyrazinyl group which is optionally monosubstituted or disubstituted by halogen atoms, $C_1$–$C_4$-alkyl or trifluoromethyl, trifluoromethoxy, hydroxyl, $C_1$–$C_4$-alkoxy, amino, monomethylamino, dimethylamino, cyano or nitro groups and which can be optionally fused to a benzene nucleus which can be optionally monosubstituted or disubstituted by halogen atoms or $C_1$–$C_4$-alkyl, hydroxyl, trifluoromethyl, $C_1$–$C_4$-alkoxy, amino, cyano or nitro groups and can optionally contain 1 nitrogen atom, or to a 5- or 6-membered ring which can contain 1–2 oxygen atoms,
- A is NH or oxygen,
- Y is $CH_2$, $CH_2$—$CH_2$, $CH_2$—$CH_2$—$CH_2$ or $CH_2$—$CH$,
- Z is nitrogen, carbon or CH, with it also being possible for the bond between Y and Z to be a double bond,
- and n is the number 2, 3 or 4.

These compounds of the formula I can be prepared by reacting a compound of the formula II

II

[Structure of formula II: R¹–N in tetrahydropyridine fused to thiophene with R³ and N=CH—OR⁴ substituent]

where R¹ has the abovementioned meanings, R³ is a cyano group or a $C_{1-3}$-alkyl-carboxylic ester group, and R⁴ is $C_{1-3}$-alkyl, with a primary amine of the formula III

III $H_2N$—$(CH_2)_n$—N—Y—Z—R² where R² has the abovementioned meanings, and, where appropriate, converting the resulting compound into the acid addition salt of a physiologically tolerated acid.

The reaction expediently takes place in an inert organic solvent, in particular a lower alcohol, e.g. methanol or ethanol, or a cyclic, saturated ether, in particular tetrahydrofuran or dioxane.

As a rule, the reaction takes place at from 20 to 110° C., in particular from 60 to 90° C., and has generally finished within from 1 to 10 hours.

Or, a compound of the formula II

II

[Structure of formula II: R¹–N tetrahydropyridine fused thiophene with R³ and N=CH—OR⁴]

where R¹ has the abovementioned meanings, R³ is a cyano group or a $C_{1-3}$-alkyl-carboxylic ester group, and R⁴ is $C_{1-3}$-alkyl, is reacted with a primary aminoalcohol of the formula IV

IV $H_2N$—$(CH_2)_n$—OH in an inert solvent, preferably alcohols such as ethanol, at from 60° to 120° C., in order to give the cyclization product V (X=OH)

V

[Structure of formula V: R¹–N in piperidine ring fused to thieno[2,3-d]pyrimidinone with A substituent, (CH₂)ₙ–X]

which is subsequently converted into the corresponding halogen derivative V (X=Cl, Br) using a halogenating agent, such as thionyl chloride or hydrobromic acid, in an organic solvent such as a halogenohydrocarbon or without any solvent, at from room temperature to 100° C. Finally, the halogen derivative of the formula V (X=Cl, Br) is reacted with an amine of the formula VI

VI $HN$—Y—Z—R², where Y, Z and R² have the abovementioned meanings, to give the novel end product of the formula I. This reaction proceeds most efficiently in an inert organic solvent, preferably toluene or xylene, in the presence of a base, such as potassium carbonate or potassium hydroxide, at from 60° C. to 150° C.

The novel compounds of the formula I can either be purified by recrystallization from the customary organic solvents, preferably from a lower alcohol, such as ethanol, or by means of column chromatography.

The free 3-substituted pyrido[3',4':4,5]thieno[2,3-d]-pyrimidine derivatives of the formula I can be converted, in the customary manner, into the acid addition salts of a solution using the stoichiometric quantity of the corresponding acid. Examples of pharmaceutically tolerated acids are hydrochloric acid, phosphoric acid, sulfuric acid, methanesulfonic acid, amidosulfuric acid, maleic acid, fumaric acid, oxalic acid, tartaric acid and citric acid.

The following Examples serve to clarify the invention:

A Preparation of the starting materials a) 2-Amino-3-carboethoxy-5-ethyl-4,5,6,7-tetrahydrothieno-[3,2-c]pyridine 62.9 ml (588 mmol) of ethyl cyanoacetate and 18.8 g (588 mmol) of powdered sulfur were added to 96.1 g (588 mmol) of 1-ethyl-3-piperidone x HCl in 350 ml of ethanol, and 150 ml (1080 mmol) of triethylamine were then added under a nitrogen atmosphere and while stirring thoroughly. After 0.5 h, the mixture was heated to reflux for 6 h and then left to stir at room temperature overnight. The reaction mixture was poured onto 3 l of ice water and the resulting mixture was adjusted to pH=9 and extracted twice with methylene chloride. After the organic phase had been dried and evaporated, the crude product was purified by column chromatography (silica gel, eluent methylene chloride/methanol 93/7). 29.2 g (20%) of product were isolated as slightly oily solids.

b) 2-Ethoxymethyleneamino-3-carboethoxy-5-ethyl-4,5,6,7-tetrahydrothieno[3,2-c]pyridine 0.5 ml of acetic anhydride was added to 3.8 g (14.9 mmol) of 2-amino-3-carboethoxy-5-ethyl-4,5,6,7-tetrahydrothieno-[3,2-c]pyridine in 40 ml of triethyl orthoformate, and the mixture was boiled under nitrogen and at reflux for 1 h. After the mixture had been decanted off from the insoluble black coating on the flask walls, it was then evaporated right down at 80° C. on a rotary evaporator. 3.5 g (94%) of crude product were isolated as a dark oil which is sufficiently pure for further reaction.

The 5-acetyl derivatives were prepared from 1-acetyl-3-piperidone in analogy with a) and b) (P. Krogsgaard-Larsen, H. Hjeds: Acta Chem. Scand B 30, 884 (1976)).

c) 3-(2-Hydroxyethyl)-6-ethyl-3,4,5,6,7,8-hexahydropyrido-[3',4':4,5]thieno[2,3-d]pyrimidin-4-one 5.0 ml (81 mmol) of ethanolamine were added to 17.0 g (55 mmol) of 2-ethoxymethyleneamino-3-carboethoxy-5-ethyl-4,5,6,7-tetrahydrothieno[3,2-c]pyridine in 130 ml of ethanol, and the mixture was boiled at reflux for 2 h. The mixture was then evaporated down to a volume of approx. 50 ml and this was thoroughly stirred in an ice bath. The fine solids which precipitated out were filtered off with suction and then washed with cold ethyl acetate. 10.5 g (63%) of a pale brown product were isolated.

d) 3-(2-Chloroethyl)-6-ethyl-3,4,5,6,7,8-hexahydropyrido-[3',4':4,5]thieno[2,3-d]pyrimidin-4-one 10.5 g (37.6 mmol) of 3-(2-hydroxyethyl)-6-ethyl-3,4,5,6,7,8-hexahydropyrido[3',4':4,5]thieno[2,3-d]pyrimidin-4-one in 100 ml of 1,2-dichloroethane were heated to reflux (slow dissolution), after which 3.5 ml (48 mmol) of thionyl chloride in 20 ml of 1,2-dichloroethane were added dropwise. After 1 h of reflux boiling, the reaction mixture was allowed to cool down and the solid was filtered off with suction; it was then rewashed with 1,2-dichloroethane. The crude product was partitioned between methylene chloride and water at pH=9. After the organic phase had been dried and concentrated, 9.3 g (83%) of product were isolated as a dark oil, which slowly crystallizes throughout and which is sufficiently pure for the subsequent reactions, m.p. 94–96° C.

e) N-(1-Naphthyl)piperazine 83.2 g (966 mmol) of piperazine, 38.0 g (339 mmol) of potassium tert-butoxide and 50.0 g (241 mmol) of 1-bromonaphthalene were added to a mixture of 5.4 g (24.2 mmol) of palladium acetate and 14.7 g (48.3 mmol) of tri-o-tolylphosphine in 500 ml of xylene, and the reaction mixture was heated at reflux for 10 h under a nitrogen atmosphere and while stirring thoroughly. After that, the mixture was diluted with methylene chloride, the insoluble residues were filtered off and the filtrate was evaporated. The crude product was purified by column chromatography (silica gel, eluent THF/methanol/ammonia 85/13/2). 21.5 g (42%) of product having a m.p. of 84–86° C. were isolated.

f) N-(2-Methyl-1-naphthyl)piperazine 14.7 g (82.7 mmol) of bis(2-chloroethyl)amine×HCl were added to 13.0 g (82.7 mmol) of 1-amino-2-methylnaphthalene in 100 ml of chlorobenzene, and the mixture was boiled under nitrogen and at reflux for 90 h. The mixture was subsequently evaporated and the residue was partitioned between methylene chloride and water at pH=9; the organic phase was then evaporated after having been dried. The crude product was purified by column chromatography (silica gel, eluent THF/methanol/ammonia 85/13/2. 11.6 g (62%) of product were isolated.

g) 4-Piperazin-1-ylisoquinoline 4.51 g (21.7 mmol) of 4-bromoisoquinoline, 4.65 g (25.0 mmol) of t-butyl piperazine-N-carboxylate, 0.1 g (0.11 mmol) of tris(dibenzylideneacetone)dipalladium, 0.11 g (0.18 mmol) of 2,2'-bis(diphenylphosphino)-1,1'-binaphthyl and 2.92 g (30.4 mmol) of sodium tert-butoxide were together added to 50 ml of toluene and the mixture was stirred at 75° C. for 2 h. The reaction mixture was added to ice/sodium chloride and the resulting mixture was extracted with ethyl acetate; the organic phase was then dried over sodium sulfate and the solvent was removed on a rotary evaporator. The product crystallized out and was filtered off with suction and washed with pentane. 5.5 g (81%) of the Boc-protected piperazine were obtained (m.p.: 111° C.). 5.2 g (16.6 mmol) of this substance were taken up in 17 ml of dichloromethane, after which 17 ml (0.22 mmol) of trifluoroacetic acid were added slowly at 0° C. The mixture was left to stir at 0° C. for 4 h, after which it was poured onto ice water and the resulting mixture was extracted with dichloromethane. The aqueous phase was filtered, rendered alkaline and then extracted with dichloromethane. After having dried over sodium sulfate and to a large extent having removed the solvent, dilution was effected with diethyl ether and the hydrochloride was precipitated with ethereal hydrochloric acid. 3.2 g (67%) of the product, having a m.p. of 293–294° C., were obtained.

Insofar as they were not known from the literature, additional piperazine derivatives (see Examples) were prepared in analogy with e), f) and g) (cf. Patent Application DE 19636769.7 as well).

B Preparation of the end products

EXAMPLE 1

3,4,5,6,7,8-Hexahydro-6-ethyl-3-[2-(4-(2-methoxyphenyl)-piperazin-1-yl)ethyl]pyrido[3',4':4,5]thieno[2,3-d]pyrimidin-4-one×3 HCl×2H$_2$O 2.3 g (10.0 mmol) of 1-(2-aminoethyl)-4-(2-methoxyphenyl)-piperazine were added to 3.1 g (10.0 mmol) of 2-ethoxymethyleneamino-3-carboethoxy-5-ethyl-4,5,6,7-tetrahydrothieno[3,2-c]pyridine in 50 ml of ethanol, and the mixture was boiled at reflux for 1 h. After that, the mixture was evaporated on a rotary evaporator and the crude product was purified by column chromatography (silica gel, eluent methylene chloride/methanol 93/7). 2.9 g (48%) of product, having a m.p. of 172–174° C., were isolated following conversion into the hydrochloride in ethyl acetate.

EXAMPLE 2

3,4,5,6,7,8-Hexahydro-6-ethyl-3-[2-(4-(2-methoxy-1-naphthyl)-piperazin-1-yl)ethyl]pyrido[3',4':4,5]thieno[2,3-d]pyrimidin-4-one×2 HCl×2 H$_2$O 1.3 g (4.5 mmol) of N-(2-methoxy-1-naphthyl)piperazine and 0.65 g (4.5 mmol) of finely powdered potassium carbonate were added to 1.1 g (4.5 mmol) of 3-(2-chloroethyl)-6-ethyl-3,4,5,6,7,8-hexahydropyrido[3',4':4,5]thieno[2,3-d]pyrimidin-4-one in 40 ml of xylene, and the mixture was boiled under a nitrogen atmosphere and at reflux for a total of 70 h. The mixture was then evaporated under reduced pressure and the residue was partitioned at pH=10 between methylene chloride and water. After the organic phases had been dried and evaporated, the crude product was purified by column chromatography (silica gel, eluent acetone). 1.1 g (50%) of product having a m.p. of 232–234° C. (decomp.), were isolated.

The following were prepared in analogy with Examples 1 and 2:

1. 3,4,5,6,7,8-Hexahydro-6-ethyl-3-[2-(4-(2-methyl-1-naphthyl)-piperazin-1-yl)ethyl]pyrido[3',4':4,5]thieno[2,3-d]-pyrimidin-4-one×2 HCl×3 H₂O, m.p. 238–240° C. (decomp.)
2. 3,4,5,6,7,8-Hexahydro-6-ethyl-3-[2-(4-(1-naphthyl)piperazin-1-yl)ethyl]pyrido[3',4':4,5]thieno[2,3-d]pyrimidin-4-one×2HCl×3 H₂O, m.p. 298–300° C. (decomp.)
3. 3,4,5,6,7,8-Hexahydro-6-ethyl-3-[2-(4-(2-methylphenyl)-piperazin-1-yl)ethyl]pyrido[3',4':4,5]thieno[2,3-d]-pyrimidin-4-one
4. 3,4,5,6,7,8-Hexahydro-6-ethyl-3-[2-(4-(2,3-dimethylphenyl)-piperazin-1-yl)ethyl]pyrido[3',4':4,5]thieno[2,3-d]-pyrimidin-4-one
5. 3,4,5,6,7,8-Hexahydro-6-ethyl-3-[2-(4-(2-chlorophenyl)-piperazin-1-yl)ethyl]pyrido[3',4':4,5]thieno[2,3-d]-pyrimidin-4-one, m.p. 148–150° C.
6. 3,4,5,6,7,8-Hexahydro-6-ethyl-3-[2-(4-pyrimidin-2-yl-piperazin-1-yl)ethyl]pyrido[3',4':4,5]thieno[2,3-d]-pyrimidin-4-one
7. 3,4,5,6,7,8-Hexahydro-6-ethyl-3-[2-(4-pyridin-2-ylpiperazin-1-yl)ethyl]pyrido[3',4':4,5]thieno[2,3-d]pyrimidin-4-one
8. 3,4,5,6,7,8-Hexahydro-6-ethyl-3-[2-(4-quinolin-2-ylpiperazin-1-yl)ethyl]pyrido[3',4':4,5]thieno[2,3-d]pyrimidin-4-one
9. 3,4,5,6,7,8-Hexahydro-6-ethyl-3-[2-(4-(2-methoxyphenyl)-piperidin-1-yl)ethyl]pyrido[3',4':4,5]thieno[2,3-d]-pyrimidin-4-one
10. 3,4,5,6,7,8-Hexahydro-6-ethyl-3-[2-(4-(2-methoxyphenyl)-3,4-dehydropiperidin-1-yl)ethyl]pyrido[3',4':4,5]thieno[2,3-d]-pyrimidin-4-one
11. 3,4,5,6,7,8-Hexahydro-6-ethyl-3-[3-(4-pyrimidin-2-yl-piperazin-1-yl)propyl]pyrido[3',4':4,5]thieno[2,3-d]-pyrimidin-4-one×3 HCl×4 H₂O, m.p. 211–213° C. (decomp.)
12. 3,4,5,6,7,8-Hexahydro-6-ethyl-3-[2-(4-tetralin-5-yl-piperazin-1-yl)ethyl]pyrido[3',4':4,5]thieno[2,3-d]pyrimidin-4-one, m.p. 287° C. (hydrochloride)
13. 3,4,5,6,7,8-Hexahydro-6-ethyl-3-[2-(4-indan-1-ylpiperazin-1-yl)ethyl]pyrido[3',4':4,5]thieno[2,3-d]pyrimidin-4-one
14. 3,4,5,6,7,8-Hexahydro-6-ethyl-3-[2-(4-(3-trifluoromethylphenyl)piperazin-1-yl)ethyl]pyrido[3',4':4,5]thieno-[2,3-d]pyrimidin-4-one×2 HCl×H₂O, m.p. 138–140° C.
15. 3,4,5,6,7,8-Hexahydro-6-ethyl-3-[2-(4-(2-cyanophenyl)-piperazin-1-yl)ethyl]pyrido[3',4':4,5]thieno-[2,3-d]pyrimidin-4-one
16. 3,4,5,6,7,8-Hexahydro-6-ethyl-3-[2-(4-isoquinolin-4-yl-piperazin-1-yl)ethyl]pyrido[3',4':4,5]thieno[2,3-d]pyrimidin-4-one
17. 3,4,5,6,7,8-Hexahydro-6-ethyl-3-[2-(4-naphth-1-ylhexahydro-1,4-diazepin-1-yl)ethyl]pyrido[3',4':4,5]thieno[2,3-d]-pyrimidin-4-one, m.p. 276–280° C. (hydrochloride)
18. 3,4,5,6,7,8-Hexahydro-6-ethyl-3-[2-(4-naphth-1-yl-3,4-dehydropiperidin-1-yl)ethyl]pyrido[3',4':4,5]thieno-[2,3-d]pyrimidin-4-one, MS: m⁺=507.1
19. 3,4,5,6,7,8-Hexahydro-6-ethyl-3-[2-(4-naphth-1-ylpiperidin-1-yl)ethyl]pyrido[3',4':4,5]thieno[2,3-d]pyrimidin-4-one
20. 3,4,5,6,7,8-Hexahydro-6-ethyl-3-[2-(4-(2-methoxynaphth-1-yl-3,4-dehydropiperidin-1-yl)ethyl]pyrido[3',4':4,5]thieno-[2,3-d]pyrimidin-4-one
21. 3,4,5,6,7,8-Hexahydro-6-ethyl-3-[3-(4-phenylpiperidin-1-yl)-propylpyrido[3',4':4,5]thieno[2,3-d]pyrimidin-4-one, m.p. 241° C. (hydrochloride)
22. 3,4,5,6,7,8-Hexahydro-6-acetyl-3-[2-(4-(2-methoxyphenyl)-piperazin-1-yl)ethyl]pyrido[3',4':4,5]thieno[2,3-d]-pyrimidin-4-one
23. 3,4,5,6,7,8-Hexahydro-6-acetyl-3-[2-(4-(2-methyl-1-naphthyl)-piperazin-1-yl)ethyl]pyrido[3',4':4,5]thieno[2,3-d]-pyrimidin-4-one
24. 3,4,5,6,7,8-Hexahydro-6-acetyl-3-[2-(4-(2-methoxy-1-naphthyl)piperazin-1-yl)ethyl]pyrido[3',4':4,5]thieno-[2,3-d]pyrimidin-4-one The acetyl group in the 6 position can, in analogy with DE 19 636 769.7, be eliminated with 10 percent hydrochloric acid, while boiling under reflux, to give the corresponding secondary amines. The alkylations at N-6 to give the 6-alkyl derivatives can likewise be performed as described in DE 19 636 769.7.

25. 3,4,5,6,7,8-Hexahydro-3-[2-(4-(2-methoxyphenyl)piperazin-1-yl)ethyl]pyrido[3',4':4,5]thieno[2,3-d]pyrimidin-4-one
26. 3,4,5,6,7,8-Hexahydro-6-benzyl-3-[2-(4-(2-methylphenyl)-piperazin-1-yl)ethyl]pyrido[3',4':4,5]thieno[2,3-d]pyrimidin-4-one
27. 3,4,5,6,7,8-Hexahydro-6-(4-chlorophenyl-2-ethyl)-3-[2-(4-(1-naphthyl)piperazin-1-yl)ethyl]pyrido[3',4':4,5]-thieno[2,3-d]pyrimidin-4-one
28. 3,4,5,6,7,8-Hexahydro-6-(4-methoxybenzyl)-3-[2-(4-(2-methyl-1-naphthyl)piperazin-1-yl)ethyl]pyrido[3',4':4,5]thieno-[2,3-d]pyrimidin-4-one
29. 3,4,5,6,7,8-Hexahydro-6-benzyl-3-[2-(4-(1-naphthyl)piperazin-1-yl)ethyl]pyrido[3',4':4,5]thieno[2,3-d]pyrimidin-4-one×2 HCl×H₂O, m.p. 268–270° C.

These compounds are suitable for treating central nervous system-related emotional disturbances such as seasonal affective disturbances and dysthymia. These disturbances also include anxiety states such as generalized anxiety, panic attacks, sociophobia, obsessional neuroses and post-traumatic stress symptoms, disturbances of the memory, including dementia, amnesias and age-related loss of memory, and also psychogenic eating disturbances such as anorexia nervosa and bulimia nervosa.

It has now been found that pyrimidine derivatives of the formula I

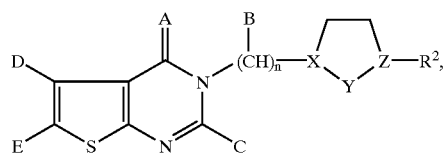

where
A is NH or oxygen,
B is hydrogen or methyl,

C is hydrogen, methyl or hydroxyl,
D is methyl, $$-\underset{\underset{O}{\|}}{C}-NR^3R^4 \quad \text{or}$$

D and E are together —$CH_2$—$CH_2$—$NR^1$—$CH_2$—, —$CH_2$—$NR^1$—$CH_2$— or —$CH_2$—$NR^1$—$CH_2$—$CH_2$—, X is nitrogen, Y is $CH_2$, $CH_2$—$CH_2$, $CH_2$—$CH_2$—$CH_2$ or $CH_2$—CH, Z is nitrogen, carbon or CH, with it also being possible for the bond between Y and Z to be a double bond, n is the number 2, 3 or 4, $R^1$ is hydrogen, a $C_1$–$C_4$-alkyl group, an acetyl or benzoyl group, a phenylalkyl $C_1$–$C_4$ radical or phenylalkoxy $C_2$–$C_5$ radical, with the aromatic moiety optionally being substituted by halogen, or $C_1$–$C_4$-alkyl, trifluoromethyl, hydroxyl, $C_1$–$C_4$-alkoxy, amino, cyano or nitro groups, a naphthylalkyl $C_1$–$C_3$ radical, a phenylalkanone $C_2$–$C_4$ radical or a phenyl- or pyridylcarbamoylalkyl $C_2$ radical, with it being possible for the phenyl or pyridyl group to be substituted by halogen, a $C_1$–$C_3$-alkyl group, a methoxy group and by a nitro or amino group, $R^2$ is a phenyl, pyridyl, pyrimidinyl or pyrazinyl group which is optionally monosubstituted, disubstituted or trisubstituted by halogen atoms, $C_1$–$C_4$-alkyl or trifluoromethyl, trifluoromethoxy, hydroxyl, $C_1$–$C_4$-alkoxy, amino, monomethylamino, dimethylamino, cyano or nitro groups and which can optionally be fused to a benzene nucleus which can optionally be monosubstituted or disubstituted by halogen atoms, $C_1$–$C_4$-alkyl or hydroxyl, trifluoromethyl, $C_1$–$C_4$-alkoxy, amino, cyano or nitro groups and which can optionally contain 1 nitrogen atom, or to a 5- or 6-membered ring which can contain 1–2 oxygen atoms, or can be substituted by a phenyl-$C_1$–$C_2$-alkyl- or -alkoxy group, with it being possible for the phenyl radical to be substituted by halogen, or a methyl, trifluoromethyl or methoxy group, $R^3$ and $R^4$ are, independently of each other, hydrogen or a $C_1$–$C_4$-alkyl group, and their physiologically tolerated salts, are suitable for producing medicaments for the prophylaxis and therapy of neurodegeneration, brain trauma and cerebral ischemia, in particular strokes, or for the prophylaxis and therapy of the sequelae which are caused by these diseases.

A use according to the invention also concerns neuroprotection.

The preparation of these pyrimidine derivatives is described in the patent specifications which were mentioned at the outset.

A medicament is produced using a compound of the formula I, or its pharmacologically tolerated acid addition salt, as the active compound, together with customary excipients and diluents.

The use according to the invention can be effected, in the customary manner, orally or parenterally, intravenously or intramuscularly.

The dose depends on the age, condition and weight of the patient and on the type of administration. As a rule, the daily dose of active compound is from about 1 to 100 mg/kg of body weight in the case of oral administration and from 0.1 to 10 mg/kg of body weight in the case of parenteral administration.

The medicaments can be used in the usual pharmaceutical administration forms in the solid or liquid state, e.g. as tablets, film tablets, capsules, powders, granules, coated tablets, suppositories, solutions, ointments, creams or sprays. These forms are produced in the customary manner. In this context, the active compounds can be worked up with the customary pharmaceutical auxiliary substances such as tablet binders, fillers, preservatives, tablet disintegrants, flow regulators, plasticizers, crosslinking agents, dispersants, emulsifiers, solvents, delayed release agents, antioxidants and/or propellant gases (cf. H. Sucker et. al: Pharmazeutische Technologie (Pharmaceutical Technology), Thieme-Verlag, Stuttgart, 1978). The resulting administration forms normally comprise the active compound in a quantity of from 1 to 99% by weight.

What is claimed is:

1. A method of preventing or treating cerebral ischemia or strokes in a mammal in need of such treatment comprising administering to said mammal an effective amount of pyrimidine derivatives of the formula I $$\underset{E}{\overset{D}{\underset{|}{\diagdown}}}\underset{S}{\overset{A}{\diagup}}\underset{N}{\overset{B}{\diagup}}(CH)_n-X\underset{Y}{\diagdown}Z-R^2,$$

where

A is NH or oxygen,

B is hydrogen or methyl,

C is hydrogen, methyl or hydroxyl,

D is methyl,

E is $$-\underset{\underset{O}{\|}}{C}-NR^3R^4 \quad \text{or}$$

D and E are together —$CH_2$—$CH_2$—$NR^1$—$CH_2$—, —$CH_2$—$NR^1$—$CH_2$— or —$CH_2$—$NR^1$—$CH_2$—$CH^2$—, X is nitrogen, Y is $CH_2$, $CH_2$—$CH_2$, $CH_2$—$CH_2CH_2$ or $CH_2$—CH, Z is nitrogen, carbon or CH, with it also being possible for the bond between Y and Z to be a double bond, n is the number 2, 3, or 4, $R^1$ is hydrogen, a $C_1$–$C_4$-alkyl group, an acetyl or benzoyl group, a phenylalkyl $C_1$–$C_4$ radical or phenylalkoxy $C_2$–$C_5$ radical, with the aromatic moiety optionally being substituted by halogen, or $C_1$–$C_4$-alkyl, trifluoromethyl, hydroxyl, $C_1$–$C_4$-alkoxy, amino, cyano or nitro groups, a naphthylalkyl $C_1$–$C_3$ radical, a phenylalkanone $C_2$–$C_4$ radical or a phenyl- or pyridylcarbamoylalkyl $C_2$ radical, with it being possible for the phenyl or pyridyl group to be substituted by halogen, a $C_1$–$C_3$-alkyl group, a methoxy group and by a nitro or amino group, $R^2$ is a phenyl, pyridyl, pyrimidinyl or pyrazinyl group which is optionally monosubstituted, disubstituted or trisubstituted by halogen atoms, $C_1$–$C_4$-alkyl or trifluoromethyl, trifluoromethoxy, hydroxyl, $C_1$–$C_4$-alkoxy, amino, monomethylamino, dimethylamino, cyano, thiomethyl or nitro groups and which can optionally be fused to a benzene nucleus which can optionally be monosubstituted or disubstituted by halogen atoms, $C_1$–$C_4$-alkyl or hydroxyl, trifluoromethyl, $C_1$–$C_4$-alkoxy, amino, cyano or nitro groups and which can optionally contain 1 nitrogen atom, or to a 5- or 6-membered ring which can contain 1–2 oxygen atoms, or can be substituted by a phenyl-$C_1$–$C_2$-alkyl- or -alkoxy group, with it being possible for the phenyl radical to be substituted by halogen, or a methyl, trifluoromethyl or methoxy group, $R^3$ and $R^4$ are, independently of each other, hydrogen or a $C_1$–$C_4$-alkyl group, or their physiologically tolerated salts.

\* \* \* \* \*